United States Patent
Chen et al.

(10) Patent No.: US 12,037,637 B2
(45) Date of Patent: Jul. 16, 2024

(54) PHOTOSELECTIVE NON-INVASIVE TARGETED GENOMIC AND EPIGENOMIC SEQUENCING OF SPATIALLY-DEFINED CELLS OR SUBCELLULAR REGIONS

(71) Applicants: THE BROAD INSTITUTE, INC., Cambridge, MA (US); PRESIDENT AND FELLOWS OF HARVARD COLLEGE, Cambridge, MA (US)

(72) Inventors: Fei Chen, Cambridge, MA (US); Sarah Mangiameli, Cambridge, MA (US); Haiqi Chen, Cambridge, MA (US)

(73) Assignees: The Broad Institute, Inc., Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/582,102

(22) Filed: Jan. 24, 2022

(65) Prior Publication Data
US 2022/0235396 A1    Jul. 28, 2022

Related U.S. Application Data

(60) Provisional application No. 63/141,342, filed on Jan. 25, 2021.

(51) Int. Cl.
*C12Q 1/686* (2018.01)
*C12N 9/22* (2006.01)
*G01N 1/30* (2006.01)

(52) U.S. Cl.
CPC .............. *C12Q 1/686* (2013.01); *C12N 9/22* (2013.01); *G01N 1/30* (2013.01)

(58) Field of Classification Search
CPC ........ C12Q 1/686; C12Q 1/6806; C12N 9/22; C12N 15/10; G01N 1/30
See application file for complete search history.

(56) References Cited

U.S. PATENT DOCUMENTS

2017/0253876 A1* 9/2017 Eberwine ............... B01J 35/004

FOREIGN PATENT DOCUMENTS

WO    WO-2011006075 A1 *  1/2011 ......... C12N 15/1048

OTHER PUBLICATIONS

Jamur, Maria Célia, and Constance Oliver. "Permeabilization of cell membranes." Immunocytochemical methods and protocols (2010): 63-66 (Year: 2010).*
Chen, Chuming, et al. "Software for pre-processing Illumina next-generation sequencing short read sequences." Source code for biology and medicine 9.1 (2014): 1-11 (Year: 2014).*
Ruble, Brittani K., Sean B. Yeldell, and Ivan J. Dmochowski. "Caged oligonucleotides for studying biological systems." Journal of inorganic biochemistry 150 (2015): 182-188 (Year: 2015).*
Picelli, Simone, et al. "Tn5 transposase and tagmentation procedures for massively scaled sequencing projects." Genome research 24.12 (2014): 2033-2040 (Year: 2014).*
Fuchs, Ryan T., et al. "Bias in ligation-based small RNA sequencing library construction is determined by adaptor and RNA structure." PloS one 10.5 (2015): e0126049 (Year: 2015).*
Ghrebi, Salem S., Gethin Rh Owen, and Donald M. Brunette. "Triton X-100 pretreatment of LR-white thin sections improves immunofluorescence specificity and intensity." Microscopy Research and Technique 70.7 (2007): 555-562 (Year: 2007).*
Buenrostro, Jason D., et al. "ATAC-seq: a method for assaying chromatin accessibility genome-wide." Current protocols in molecular biology 109.1 (2015): 21-29 (Year: 2015).*
Lee J. et al. Single Cell Spatial Chromatin Analysis of Fixed Immunocytochemically Identified Neuronal Cells. bioRxiv 780387; doi: https://doi.org/10.1101/780387.
Genshaft A.S. et al. Spatially-Resolved Live Cell Tagging and Isolation Using Protected Photoactivatable Cell Dyes. bioRxiv 2020.02.28.966598; doi: https://doi.org/10.1101/2020.02.28.966598.
Curran S., McKay J.A., McLeod H.L., Murray G.I. Laser capture microscopy. Mol Pathol. 2000;53(2):64-68. doi:10.1136/mp.53.2.64.

* cited by examiner

*Primary Examiner* — Nancy J Leith
*Assistant Examiner* — Kyle Thomas Rega
(74) *Attorney, Agent, or Firm* — Withers Bergman LLP; Richard B Emmons; Christopher R. Cowles

(57) ABSTRACT

The present disclosure relates to methods aimed towards non-invasive targeted genomic and epigenomic sequencing of spatially-defined cellular or subcellular region. More particularly, the present disclosure relates to methods of using photoselection to achieve non-invasive targeted genomic and epigenomic sequencing of spatially-defined cellular or subcellular regions, via the use of light-activated probes.

18 Claims, 6 Drawing Sheets
Specification includes a Sequence Listing.

PHOTOSELECTIVE NON-INVASIVE TARGETED GENOMIC AND EPIGENOMIC SEQUENCING OF SPATIALLY-DEFINED CELLS OR SUBCELLULAR REGIONS

CROSS-REFERENCE TO RELATED APPLICATION

The present application is related to and claims priority under 35 U.S.C. § 119(e) to U.S. provisional patent application No. 63/141,342, entitled "Photoselective Non-Invasive, Targeted Genomic and Epigenomic Sequencing of Spatially-Defined Cells or Subcellular Regions," filed Jan. 25, 2021. The entire content of the aforementioned patent application is incorporated herein by this reference.

FIELD OF THE DISCLOSURE

The present disclosure relates to methods aimed towards non-invasive targeted genomic and epigenomic sequencing of spatially-defined cellular or subcellular regions. More particularly, the present disclosure relates to methods of using photoselection for non-invasive targeted genomic and epigenomic sequencing of spatially-defined cellular or subcellular regions using light-activated probes.

SEQUENCE LISTING

The instant application contains a Sequence Listing which has been filed electronically in ASCII format and is hereby incorporated by reference in its entirety. Said ASCII copy, created on Jan. 24, 2022 is named BN00007_1321_BI10783_SeqListing.txt and is 2,275 bytes in size.

BACKGROUND OF THE DISCLOSURE

While advancements in methods to effectively profile genomic and epigenomic features have increasingly provided deeper understanding of cell development and disease, such methods, including established DNA sequencing library preparations, usually require cellular dissociation, and are insensitive to morphological features such as the arrangement of cells within a tissue or subcellular structures. Previous methods for collecting DNA from specific spatial regions, such as laser capture and CHEX-seq (chromatin exposed sequencing), have confronted challenges such as a contamination from neighboring cells during targeted cell excision, inability to achieve subcellular resolutions, lack of tractability for dispersed target cells, and a lack of versatility to measure multiple features from the sample. Accordingly, a need exists for new methods that are capable of effectively profiling genomic and epigenomic features while maintaining sensitivity to the native cellular microenvironment.

BRIEF SUMMARY OF THE DISCLOSURE

The current disclosure relates, at least in part, to methods for non-invasive targeted genomic and epigenomic sequencing of spatially-defined cellular or subcellular region(s) using light activated probes that provide for photoselective sequencing. Specifically contemplated applications for the non-invasive targeted genomic and epigenomic sequencing of spatially-defined cellular or subcellular regions using light activated probes that the instant disclosure provides include, without limitation, targeted ATAC-seq (Assay for Transposase-Accessible Chromatin using sequencing) for profiling of open chromatin regions restricted to a desired population of cells, and selective analysis of protein-DNA interactions by selectively probing the genomic locations of protein complexes with particular spatial features, as visualized by fluorescence microscopy. A wide range of diagnostic, therapeutic and research applications are therefore contemplated.

In one aspect, the disclosure provides a method for obtaining targeted genomic and epigenomic sequence data from a tissue or cell sample that includes the steps of: (i) obtaining the tissue or cell sample from a subject; (ii) fixing the tissue or cell sample with a fixing agent; (iii) staining the fixed tissue or cell sample; (iv) preparing a photolabile sequencing library using a DNA fragmenting agent loaded with amplification-blocked adapters; (v) targeting illumination of the fixed tissue or cell sample with near-UV light to unblock the adapters in a region of interest; (vi) purifying DNA from the sample; and (vii) amplifying and sequencing the unblocked adapters on a sequencing platform.

In some embodiments, the method further includes the step of: permeabilizing the fixed tissue or cell sample of step (ii) with a permeabilizing agent.

In some embodiments, the amplification-blocked adapters include an oligonucleotide sequence conjugated to a fluorophore via a photocleavable spacer.

In some embodiments, the photocleavable spacer includes a photolabile molecule that is cleaved during exposure to light in the near-ultraviolet spectral range.

In some embodiments, the photocleavable spacer comprises a 10 atom long molecule which is cleaved upon absorption of near-ultraviolet light to produce an exposed 5'phosphate.

In certain embodiments, secondary adapter sequences are selectively ligated to unblocked adapters prior to step (vii) amplifying and sequencing the unblocked adapters on a sequencing platform.

In some embodiments, the permeabilizing agent is selected from among the following: Triton X-100, NP-40, methanol, acetone, Tween 20, saponin, Leucoperm™, and digitonin.

In some embodiments, the permeabilizing agent is Triton X-100 at a concentration between about 0.01% and about 5%.

In some embodiments, contacting of the section of the tissue sample with the permeabilizing agent is performed for a duration of time between about 0.1 minute and about 30 minutes.

In some embodiments, the DNA fragmenting agent is selected from among the following: a transposase; $H_2O_2$; sonication; and a DNase. Optionally, the DNase is a restriction endonuclease.

In some embodiments, the DNA fragmenting agent includes a Tn5 transposase enzyme. Optionally, the Tn5 transposase enzyme is present in a tagmentation buffer including adapter and mosaic oligonucleotides.

In some embodiments, the Tn5 enzyme in tagmentation buffer including adapter and mosaic oligonucleotides contacts the sectioned tissue sample for about 20 minutes to about 16 hours. Optionally, the Tn5 enzyme in tagmentation buffer including adapter and mosaic oligonucleotides contacts the sectioned tissue sample at between about 25° C. and about 55° C.

In embodiments, the section of the tissue sample is a fixed section or a cryosection.

In some embodiments, the target DNA molecules are selected from among the following: genomic DNA molecules, mitochondrial DNA (mtDNA) molecules, viral DNA molecules (optionally retroviral DNA molecules or AAV DNA molecules) and bacterial DNA molecules.

In embodiments, the target DNA molecules are genomic DNA molecules. Optionally, the genomic DNA molecules are enriched for accessible chromatin sequences, as compared to inaccessible chromatin sequences (e.g., genomic DNA sequences associated with nucleosomes and/or other forms of condensed chromatin).

In some embodiments, the permeabilizing agent is about 0.1% to about 0.5% Triton X-100. Optionally, the contacting of the section of the tissue sample with the Triton X-100 is performed for a duration of time between about 10 minutes and about 60 minutes.

In certain embodiments, the tissue sample is obtained from a tissue selected from among the following: brain, lung, liver, kidney, pancreas, heart, and gastrointestinal (GI) tract.

In embodiments, the tissue sample is obtained from a tumor.

In some embodiments, the subject is a mammal. Optionally, the subject is a human.

In embodiments, the sequencing platform is a NGS platform. Optionally, the NGS platform is an Illumina® platform.

In some embodiments, the method is compatible with established Tn5-transposase based library preparations including ATAC-seq, Cut & Tag, or whole-genome sequencing.

In embodiments, the method further includes the step (x) generating an image of the tissue sample that depicts the location(s) and relative abundance of one or more captured target DNAs within the sample. Optionally, the image is a two-dimensional image.

In an aspect, the disclosure provides a method for non-invasive targeted genomic and epigenomic sequencing of a spatially-defined cellular or subcellular region using light-activated probes, the method including the steps of: (i) obtaining cells or a tissue sample from a subject; (ii) fixing and permeabilizing the cells or the tissue sample with a fixing agent and a permeabilizing agent; (iii) staining the fixed cells or tissue sample to visualize one or more regions of interest by microscopy; (iv) preparing a photolabile sequencing library using Tn5 transposase enzyme loaded with amplification-blocked adapters, where the adapters include an oligonucleotide sequence conjugated to a fluorophore via a photocleavable spacer; (v) targeting illumination of the fixed cells or tissue sample with near-UV light to unblock the adapters in the one or more regions of interest; (vi) purifying DNA from the sample; and (vii) amplifying and sequencing the unblocked adapters on a sequencing platform.

In some embodiments, the Tn5 transposase enzyme loaded with amplification-blocked adapters is present in a tagmentation buffer.

In some embodiments, the Tn5 enzyme loaded with amplification-blocker adapters in tagmentation buffer contacts the sectioned tissue sample for about 20 minutes to about 16 hours, optionally wherein the Tn5 enzyme loaded with customized amplification-blocker adapters in tagmentation buffer contacts the sectioned tissue sample at between about 25° C. and about 55° C.

In some embodiments, the buffer contacts the sectioned tissue sample for about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, or about 16 hours.

In some embodiments, the tissue sample is obtained from a tissue selected from the group consisting of brain, lung, liver, kidney, pancreas, heart, and gastrointestinal (GI) tract.

In some embodiments, the tissue sample is obtained from a tumor.

In some embodiments, the subject is a mammal, optionally a human.

In some embodiments, the sequencing platform is an Illumina® platform.

In an aspect, the disclosure provides a kit for non-invasive targeted genomic and epigenomic sequencing of a spatially-defined cellular or subcellular region using light activated probes that includes: (i) a permeabilizing agent; and (ii) a DNA fragmenting agent loaded with amplification-blocked adapters.

In some embodiments, the permeabilizing agent is Triton X-100 at a concentration between about 0.01% and about 5%.

In some embodiments, the DNA fragmenting agent is selected from the group consisting of a transposase; $H_2O_2$; sonication; and a DNase, optionally wherein the DNase is a restriction endonuclease.

In some embodiments, the DNA fragmenting agent comprises a Tn5 transposase enzyme, optionally wherein the Tn5 transposase enzyme is present in a tagmentation buffer.

In some embodiments, the amplification-blocked adapters include an oligonucleotide sequence conjugated to a fluorophore via a photocleavable spacer.

In certain embodiments, the kit includes secondary adapters for ligation to unblocked adapters.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), multiple displacement amplification (MDA), ligation extension, or ligation chain reaction. An amplicon can be a nucleic acid molecule having a single copy of a particular nucleotide sequence (e.g., a PCR product) or multiple copies of the nucleotide sequence (e.g., a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "array" refers to a population of features or sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells, beads arranged upon a flat surface (e.g., a slide), optionally beads captured upon a flat surface (e.g., a layer of beads adhered to or otherwise stably associated with a slide (e.g., a layer of beads adsorbed to a slide-attached elastomeric surface)), etc.

As used herein, the term "attached" refers to the state of two things being joined, fastened, adhered, connected or bound to each other. For example, an analyte, such as a nucleic acid, can be attached to a material, such as a gel or solid support, by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "barcode sequence" is intended to mean a series of nucleotides in a nucleic acid that can be used to identify the nucleic acid, a characteristic of the nucleic acid (e.g., the identity and optionally the location of a bead to which the nucleic acid is attached), or a manipulation that has been carried out on the nucleic acid. The barcode sequence can be a naturally occurring sequence or a sequence that does not occur naturally in the organism from which the barcoded nucleic acid was obtained. A barcode sequence can be unique to a single nucleic acid species in a population or a barcode sequence can be shared by several different nucleic acid species in a population (e.g., all nucleic acid species attached to a single bead might possess the same barcode sequence, while different beads present a different shared barcode sequence that serves to identify each such different bead). By way of further example, each nucleic acid probe in a population can include different barcode sequences from all other nucleic acid probes in the population. Alternatively, each nucleic acid probe in a population can include different barcode sequences from some or most other nucleic acid probes in a population. For example, each probe in a population can have a barcode that is present for several different probes in the population even though the probes with the common barcode differ from each other at other sequence regions along their length. In particular embodiments, one or more barcode sequences that are used with a biological specimen (e.g., a tissue sample) are not present in the genome, transcriptome or other nucleic acids of the biological specimen. For example, barcode sequences can have less than 80%, 70%, 60%, 50% or 40% sequence identity to the nucleic acid sequences in a particular biological specimen.

As used herein, "beads", "microbeads", "microspheres" or "particles" or grammatical equivalents can include small discrete particles. The composition of the beads can vary, depending upon the class of capture probe, the method of synthesis, and other factors. In certain embodiments of the disclosure, the sizes of the beads of the disclosure tend to range from 1 μm to 100 μm in diameter (with all subranges within this range expressly contemplated), e.g., depending upon the extent of image resolution desired, nature of the solid support to be used for spatial bead array construction, sequencing processes (e.g., flow cell sequencing) to be employed, as well as other factors.

As used herein, the term "biological specimen" is intended to mean one or more cell, tissue, organism or portion thereof. A biological specimen can be obtained from any of a variety of organisms. Exemplary organisms include, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans;* an insect such as *Drosophila melanogaster*, mosquito, fruit fly, honey bee or spider; a fish such as zebrafish; a reptile; an amphibian such as a frog or *Xenopus laevis*; a Dictyostelium discoideum; a fungi such as *Pneumocystis carinii, Takifugu rubripes*, yeast, *Saccharomyces cerevisiae* or *Schizosaccharomyces pombe*; or a *Plasmodium falciparum*. Target nucleic acids can also be derived from a prokaryote such as a bacterium, *Escherichia coli*, Staphylococci or *Mycoplasma pneumoniae*; an archae; a virus such as Hepatitis C virus or human immunodeficiency virus; or a viroid. Specimens can be derived from a homogeneous culture or population of the above organisms or alternatively from a collection of several different organisms, for example, in a community or ecosystem.

As used herein, the term "cleavage site" is intended to mean a location in a nucleic acid molecule that is susceptible to bond breakage. The location can be specific to a particular chemical, enzymatic or physical process that results in bond breakage. For example, the location can be a nucleotide that is abasic or a nucleotide that has a base that is susceptible to being removed to create an abasic site. Examples of nucleotides that are susceptible to being removed include uracil and 8-oxo-guanine as set forth in further detail herein below. The location can also be at or near a recognition sequence for a restriction endonuclease such as a nicking enzyme.

By "control" or "reference" is meant a standard of comparison. Methods to select and test control samples are within the ability of those in the art. Determination of statistical significance is within the ability of those skilled in the art, e.g., the number of standard deviations from the mean that constitute a positive result.

As used herein, the term "cryosection" refers to a piece of tissue, e.g., a biopsy, that has been obtained from a subject, snap frozen, embedded in optimal cutting temperature embedding material, frozen, and cut into thin sections. In certain embodiments, the thin sections can be treated with a permeabilizing agent and/or a DNA fragmenting agent, and then directly applied to an array of beads captured upon a solid support (e.g., a slide), or the thin sections can be fixed (e.g., in methanol or paraformaldehyde), treated with a permeabilizing agent and/or a DNA fragmenting agent, and then applied to a bead-presenting planar surface, e.g., a slide upon which a layer of microbeads has been attached/arrayed.

As used herein, the term "different", when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different for the two or more molecules while also having a universal sequence portion that is the same on the two or more molecules. Two beads can be different from each other by virtue of being attached to different nucleic acids.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "extend," when used in reference to a nucleic acid, is intended to mean addition of at least one nucleotide or oligonucleotide to the nucleic acid. In particular embodiments one or more nucleotides can be added to the 3' end of a nucleic acid, for example, via polymerase catalysis (e.g., DNA polymerase, RNA polymerase or reverse transcriptase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g., ligase catalysis) methods. A nucleic acid can be extended in a template directed manner, whereby the product of extension is complementary to a template nucleic acid that is hybridized to the nucleic acid that is extended.

As used herein, the term "feature" means a location in an array for a particular species of molecule. A feature can contain only a single molecule or it can contain a population of several molecules of the same species. Features of an array are typically discrete. The discrete features can be contiguous or they can have spaces between each other. The size of the features and/or spacing between the features can vary such that arrays can be high density, medium density or lower density. High density arrays are characterized as having sites separated by less than about 15 μm. Medium density arrays have sites separated by about 15 to 30 μm, while low density arrays have sites separated by greater than 30 μm. An array useful herein can have, for example, sites that are separated by less than 100 μm, 50 μm, 10 μm, 5 μm, 1 μm, or 0.5 μm. An apparatus or method of the present disclosure can be used to detect an array at a resolution sufficient to distinguish sites at the above densities or density ranges.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

As used herein, the term "next-generation sequencing" or "NGS" can refer to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyrosequencing (454 Life Sciences/Roche Diagnostics); solid-phase, reversible dye-terminator sequencing (Solexa/Illumina®); SOLiD™ technology (Applied Biosystems); Ion semiconductor sequencing (Ion Torrent™); and DNA nanoball sequencing (Complete Genomics). Descriptions of certain NGS platforms can be found in the following: Shendure, er al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3):333-43; and Zhang et al., "The impact of next-generation sequencing on genomics", J Genet Genomics, 201, 38(3): 95-109.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g., found in deoxyribonucleic acid (DNA)) or a ribose sugar (e.g., found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid or sequence of a nucleic acid, are intended as semantic identifiers for the nucleic acid or sequence in the context of a method or composition set forth herein and does not necessarily limit the structure or function of the nucleic acid or sequence beyond what is otherwise explicitly indicated. The terms "probe" and "target" can be similarly applied to other analytes such as proteins, small molecules, cells or the like.

As used herein, the term "random" can be used to refer to the spatial arrangement or composition of locations on a surface. For example, there are at least two types of order for an array described herein, the first relating to the spacing and relative location of features (also called "sites") and the second relating to identity or predetermined knowledge of the particular species of molecule that is present at a particular feature. Accordingly, features of an array can be randomly spaced such that nearest neighbor features have variable spacing between each other. Alternatively, the spacing between features can be ordered, for example, forming a regular pattern such as a rectilinear grid or hexagonal grid. In another respect, features of an array can be random with respect to the identity or predetermined knowledge of the species of analyte (e.g., nucleic acid of a particular sequence) that occupies each feature independent of whether spacing produces a random pattern or ordered pattern. An array set forth herein can be ordered in one respect and random in another. For example, in some embodiments set forth herein a surface is contacted with a population of nucleic acids under conditions where the nucleic acids attach at sites that are ordered with respect to their relative locations but 'randomly located' with respect to knowledge of the sequence for the nucleic acid species present at any particular site. Reference to "randomly distributing" nucleic acids at locations on a surface is intended to refer to the absence of knowledge or absence of predetermination regarding which nucleic acid will be captured at which location (regardless of whether the locations are arranged in an ordered pattern or not).

As used herein, the term "solid support" refers to a rigid substrate that is insoluble in aqueous liquid. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid supports for some embodiments are slides and beads capable of assorting/packing upon the surface of a slide (e.g., beads to which a large number of oligonucleotides are attached).

As used herein, the term "spatial tag" is intended to mean a nucleic acid having a sequence that is indicative of a location. Typically, the nucleic acid is a synthetic molecule having a sequence that is not found in one or more biological specimen that will be used with the nucleic acid. However, in some embodiments the nucleic acid molecule can be naturally derived or the sequence of the nucleic acid can be naturally occurring, for example, in a biological specimen that is used with the nucleic acid. The location indicated by a spatial tag can be a location in or on a biological specimen, in or on a solid support or a combination thereof. A barcode sequence can function as a spatial tag. In certain embodiments, the identification of the tag that serves as a spatial tag is only determined after a population of beads (each possessing a distinct barcode sequence) has been arrayed upon a solid support (optionally randomly arrayed upon a solid support) and sequencing of such a bead-associated barcode sequence has been determined in situ upon the solid support.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the term "tissue" is intended to mean an aggregation of cells, and, optionally, intercellular matter. Typically the cells in a tissue are not free floating in solution and instead are attached to each other to form a multicellular structure. Exemplary tissue types include muscle, nerve, epidermal and connective tissues.

As used herein, the term "universal sequence" refers to a series of nucleotides that is common to two or more nucleic acid molecules even if the molecules also have regions of sequence that differ from each other. A universal sequence that is present in different members of a collection of molecules can allow capture of multiple different nucleic acids using a population of universal capture nucleic acids that are complementary to the universal sequence. Similarly, a universal sequence present in different members of a collection of molecules can allow the replication or amplification of multiple different nucleic acids using a population of universal primers that are complementary to the universal sequence. Thus, a universal capture nucleic acid or a universal primer includes a sequence that can hybridize specifically to a universal sequence. Target nucleic acid molecules may be modified to attach universal adapters, for example, at one or both ends of the different target sequences.

Unless specifically stated or obvious from context, as used herein, the term "or" is understood to be inclusive. Unless specifically stated or obvious from context, as used herein, the terms "a", "an", and "the" are understood to be singular or plural.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The embodiments set forth below and recited in the claims can be understood in view of the above definitions.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 2A is an image showing photoselective ATAC libraries in HeLa cells, as visualized by a fluorescently-labeled photocleavable tagmentation adapter. Targeted illumination of specific cells cleaves the spacer, removing the fluorophore from the adapter and exposing a 5'phosphate used in subsequent steps of the library prep. This results in a loss of fluorescence. FIG. 2B is a graph showing photoselective sequencing libraries in HeLa cells have hallmark properties of ATAC including a periodic fragment size distribution and high enrichment in transcription start sites. FIG. 2C is a bar graph showing photoselective sequencing background estimated by a species mixing experiment. Mouse (M) and human (H) DNA from various numbers of cells were mixed, however only the DNA from one species was unblocked (blocked species indicated as BG). The fraction of reads mapping to the genomes of each species is shown, with >90% of reads map to the correct genome, even in the worst case. FIG. 2D show images of a photoselective ATAC library as visualized in the dentate gyrus region of the mouse brain, before and after photoselection. FIG. 2E is a scatterplot showing photoselected granule cell data compared to granule cell data from a published single cell ATAC data set. Scatter plot compares reads in peaks between the two data sets (where peaks were called on the pooled data).

DETAILED DESCRIPTION OF THE INVENTION

Figure 1:
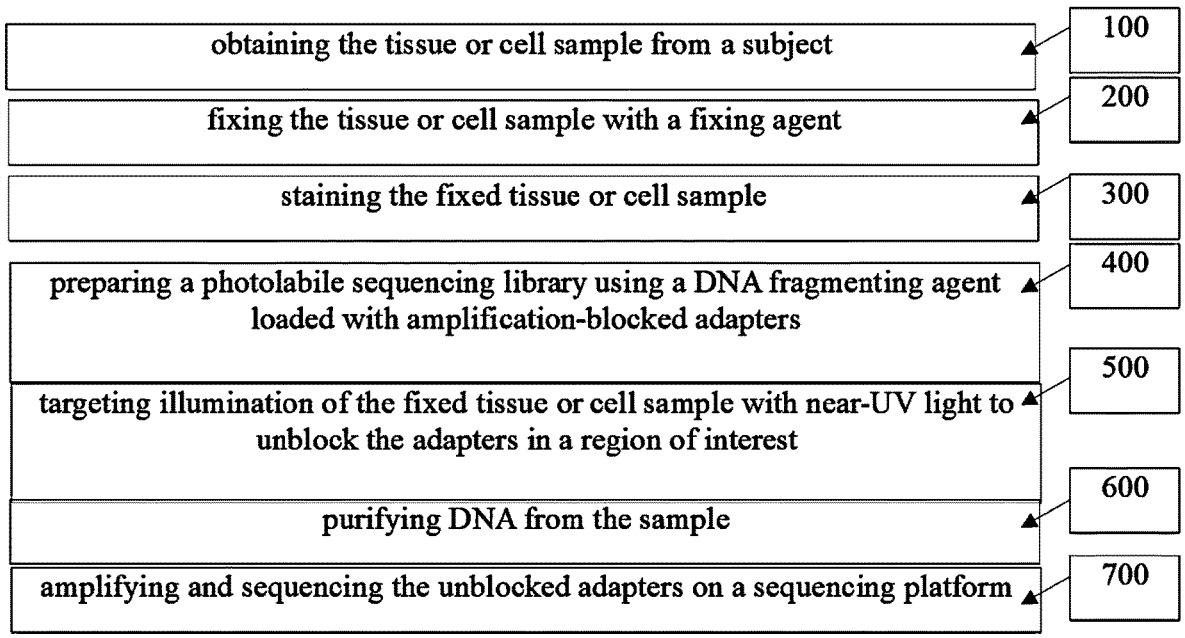
FIG. 1 illustrates a flowchart showing an exemplary method for non-invasive targeted genomic and epigenomic sequencing of spatially-defined cellular or subcellular region using light-activated probes.

The present disclosure is based, at least in part, on the discovery of photoselective sequencing, a sequencing methodology that enables non-invasive targeted genomic and epigenomic sequencing of spatially-defined cellular or subcellular regions of tissues or cell populations or cells using light-activated probes. In particular aspects, the disclosure provides in-situ tagmentation with blocked adapters consisting of an oligonucleotide sequence conjugated to a fluorophore via a photocleavable spacer. Photo-induced cleavage of the spacer removes the fluorophore and uncages a 5' phosphate group that enables ligation of secondary adapters, which are subsequently used to amplify the selected DNA fragments, optionally after digestion of the sample. Advantageously, photoselective sequencing provides diffraction-limited resolution and straightforward compatibility with varied genomic and epigenetic sequencing libraries. Additionally, photoselective sequencing is not limited to spatially localized populations of cells.

According to the techniques herein, an exemplary embodiment of photoselective sequencing may involve staining fixed tissues or populations of cells or cells to visualize regions of interest by microscopy; preparing a photolabile sequencing library via in situ tagmentation by using Tn5 transposase loaded with customized amplification-blocked adapters (e.g., oligonucleotide sequences conjugated to a fluorophore via a photocleavable spacer); illuminating with near-UV light, in a spatially targeted manner, the stained sample (e.g., fixed tissues, populations of cells, cells, and the like) to unblock the customized amplification-blocked adapters in the regions of interest (e.g., by uncaging a 5' phosphate group that enables ligation of secondary adapters); purifying the library (with total nucleic acids and/or DNA) from the sample; amplifying the un-blocked fragments (e.g., by ligating secondary adapter oligonucleotides and conducting PCR); and bulk sequencing the amplified fragments (e.g., via an Illumina® platform).

The techniques herein provide for the preparation of DNA sequencing libraries by capturing targeted double-stranded DNA sequences from spatially-defined regions within tissues or cell population with diffraction-limited resolution. The techniques herein are compatible with established Tn5-transposase based library preparations. Examples of contemplated applications for methods of non-invasive targeted genomic and epigenomic sequencing of spatially-defined cellular or subcellular region using light activated probes include, but are not limited to, targeted ATAC-seq (Assay for Transposase-Accessible Chromatin using sequencing) for profiling of open chromatin regions restricted to a desired population of cells, and selective analysis of protein-DNA interactions by selectively probing the genomic locations of protein complexes with particular spatial features, as visualized by fluorescence microscopy. A wide range of diagnostic, therapeutic and research applications are therefore contemplated.

The techniques herein employ in-situ tagmentation of a sample (e.g., a tissue sample, a cell population, cells, or the like) with blocked adapters consisting of an oligonucleotide sequence conjugated to a fluorophore (see e.g., US2020/0115753A1) via a photocleavable spacer. Cleavage of the spacer removes the fluorophore and uncages a 5' phosphate group, which enables ligation of secondary adapters that are subsequently used to amplify the selected DNA fragments after digestion of the sample. This in turn allows for the capture of cellular target DNA molecules of cryosectioned tissue in a manner that is both spatially resolvable at high resolution (e.g., generally about 200 to about 500 nm, more particularly about 200 nm, about 225 nm, about 250 nm, about 275 nm, about 300 nm, about 325 nm, about 350 nm, about 375 nm, about 400 nm, about 425 nm, about 450 nm, about 475 nm, or about 500 nm between image features) and with deep coverage. For example, high-resolution images of relative levels for individual target DNA sequences can be generated using the methods of the disclosure for a large number (e.g., tens, hundreds, thousands, millions, etc.) of DNA sequences, across an individual fixed tissue sample).

The techniques herein provide spatially resolved capture of DNA for sequencing from cells and tissues with diffraction-limited resolution of approximately 200-500 nm (sub-cellular). Art-recognized spatial profiling technologies have the disadvantage of being directed to targeted in situ techniques, which are laborious, offer only a low degree of multiplexing with a high degree of technical difficulty, and provide only very low resolution on spatial capture arrays (e.g., resolutions of approximately 100-200 µm). The disclosure provides a level of image resolution that is a full order of magnitude superior in lateral resolution to such prior approaches, and two orders of magnitude superior in capture area. By using DNA capture and subsequent high-throughput sequencing (e.g., Illumina® bead-based sequencing), the disclosure provides methods that are easily adoptable and allows for whole and partial genomic profiling of complex tissues.

Various embodiments of methods of the disclosure are considered in additional detail below.

Understanding tissue function is facilitated not only by knowledge of cell types and states but also their spatial organization within the tissue. Current technologies to investigate tissue biology fall typically into one of two categories: 1) high throughput transcriptomics and/or (epi) genomics, which capture a comprehensive snapshot of cell states within a tissue but lose the spatial context of those cells, or 2) imaging-based methods that provide spatial information but are typically laborious and require a priori knowledge of which genes/transcripts/proteins to target. Advantageously, the techniques herein provide improved technologies/platforms that allow unbiased, high-throughput capture of particularly genomic and/or mitochondrial DNA fragments from intact tissue while preserving their spatial context.

Examples of previous attempts to integrate genomics with spatial information have relied on physically separating regions of the tissue with laser capture microdissection (LCM), followed by next-generation sequencing. While this approach has provided many useful insights, its power is limited by low throughput (e.g., dissection is laborious and time consuming) and the inevitable destruction of parts of the tissue by the laser.

Recent approaches, such as "CHEX-seq" (see e.g., US Patent Publication No. 20200216841A1), have provided for targeted illumination to selectively identify single-stranded DNA with sub-cellular resolution. However, even with such approaches available, development of an improved means for non-invasively capturing targeted double-stranded DNA sequences from spatially-defined regions with high spatial resolution to prepare a DNA sequencing library was identified as likely to provide further benefit.

The disclosure provides methods for non-invasively capturing targeted double-stranded DNA sequences from spatially-defined regions of tissue (e.g., fixed tissue preparations) or cell populations to prepare a DNA sequencing library in a high-throughput manner (e.g., read-outs are obtained via next-generation sequencing) and with high (up to 10 µm, 10-100 µm, etc.) spatial resolution.

Two key concepts that distinguish the methods from many prior approaches are: 1) use of targeted illumination to non-invasively capture targeted double-stranded DNA sequences from spatially-defined regions of tissue (e.g., fixed tissue preparations) or cell populations with diffraction-limited resolution and 2) compatibility with established Tn5-transposase based library preparations such as "ATAC-seq" (see e.g., US Patent Publication No. 20180237951A1), Cut & Tag, or whole-genome sequencing. In certain aspects of the disclosure, the tissue section is treated with a permeabilizing agent and/or a DNA fragmenting agent, and is then contacted with Tn5 transposase loaded with customized amplification-blocked adapters consisting of an oligonucleotide sequence conjugated to a fluorophore via a photocleavable spacer.

According to the techniques herein, the amplification-blocked adapters have the following structure: 5'-Fluorophore-Photocleavable spacer-oligonucleotided sequence-3'. The fluorophore is chosen for compatibility with the stains in the sample and may include cyanine fluors (e.g. Cy3, Cy5, Cy7), Alexa Fluors (e.g. Alexa Fluor 488, Alexa Fluor 647), or any other small molecule fluorophore that can be conjugated via the photocleavable spacer. The photocleavable spacer is a 10 atom long molecule that is cleaved upon absorption of near-ultraviolet light. The oligonucleotide sequences typically used are as follows:

(SEQ ID NO: 1)
5'-TCGTCGGCAGCGTCAGATGTGTATAAGAGACAG-3'

(SEQ ID NO: 2)
5'-GTCTCGTGGGCTCGGAGATGTGTATAAGAGACAG-3'

However, the two adapters may have the generalized structure:

(SEQ ID NO: 3)
5'-NNNNNNNNNNNNNNNNNNNNNTGTATAAGAGACAG-3'

Where N is any of the four nucleotides A, T, C or G. The number of N nucleotides may vary as long as compatibility is maintained with the intended sequencing platform.

The "CHEX-seq" approach of US Patent Publication No. 20200216841A1 successfully demonstrated that a non-invasive targeted illumination can be utilized to selectively identify single-stranded DNA with sub-cellular resolution. The techniques herein provide several advantages over the "CHEX-seq" approach to provide enhanced access to cellular DNA, specifically by processing fixed tissue sections in a manner that allows for simultaneous readout of cellular DNA sequences and location of such DNA sequences within the tissue by next-generation sequencing (e.g., without imaging the tissue on a microscope). For example, the techniques herein provide for, but are not limited to, improved assessment of the following:

1) Mitochondrial lineage tracing. Somatic mutations in mitochondrial DNA have been recently shown to enable lineage inference in hematopoietic cells and solid tumors. Since the instant approach is capable of capturing all forms of cellular DNA, including mitochondrial DNA, it can be applied to study clonal dynamics and their spatial relationship in tissues.

2) High-resolution spatial assessment of epigenetic regulation, including, e.g., high-resolution spatial assessment of DNA methylation patterns. The previously described Assay for Transposase-Accessible Chromatin using sequencing (ATAC-seq in e.g., US Patent Publication No. 20180237951A1) has led to numerous new insights into cell state transitions and gene regulation, but has so far not been able to preserve spatial information with high resolution. Using the approach of the disclosure DNA libraries have now been successfully prepared that show a significant enrichment for transcription start sites, which indicates that the instant approach can specifically capture accessible chromatin. The disclosure can therefore be used to study how different cell types with varying epigenetic states are spatially distributed within a tissue.

3) Improved identification of regions of monoallelic gene expression and gene dosage in an assayed tissue. A variety of genes are expressed from one allele only (e.g., through imprinting, X chromosome inactivation, or autosomal random monoallelic expression) but many aspects of their regulation, such as tissue-specific skewing towards one allele or the stability of repression of autosomal alleles, are poorly understood. In certain aspects, the disclosure allows for capture specifically of accessible chromatin (i.e. active alleles), which can therefore be used to study the spatial distribution of mono- vs. bi-allelic gene expression.

5) High-resolution, spatial evaluation of gene therapy deliverables to tissue, including, e.g., identification of cellular delivery of CRISPR/Cas9 plasmid(s) and/or gels, TALEN plasmid(s) and/or gels, viral vectors (e.g., AAV), expression vectors/plasmids in general, etc.

6) Assessment of synthetic DNA arrays for sequence-specific quantities and distributions of DNA upon the synthetic DNA array. It is herein specifically contemplated that DNA from synthetic arrays can be allowed to hybridize to a sequenced puck, using known sequences attached to the DNA (so that target DNA can be captured by reverse-complement sequences included in the bead-attached oligonucleotides. Tagmentation (see e.g., US Patent Publication No. 2020/0115753 A1) as described herein is an approach that allows for addition of such adapter sequences.

Additional details of the disclosure are provided in the following sections.

Permeabilizing Agents

Certain aspects of the disclosure feature permeabilizing agents, examples of which tend to compromise and/or remove the protective boundary of lipids often surrounding cellular macromolecules. Disruption of cellular lipid barriers via administration of a permeabilizing agent can provide enhanced physical access to cellular macromolecules, such as DNA, that might otherwise be relatively inaccessible. Specifically contemplated examples of permeabilizing agents include, without limitation: Triton X-100, NP-40, methanol, acetone, Tween 20, saponin, Leucoperm™, and digitonin, among others.

DNA Fragmenting Agents

Some aspects of the disclosure employ DNA fragmenting agents, which typically allow for capture of target DNA molecules and performance of high throughput DNA sequencing upon such captured target DNA molecules (e.g., target DNA of accessible chromatin in situ). In certain embodiments for DNA preparation, a hyperactive variant of the Tn5 transposase that mediates the fragmentation of double-stranded DNA and ligates synthetic oligonucleotides at both ends can be employed. In the Tn5 tagmentation reaction, the Tn5 enzyme randomly cleaves accessible double stranded DNA into fragments and tags the DNA, by end-joining to the 5'-ends synthetic "mosaic ends," or adapter sequences. In embodiments of the disclosure, the mosaic ends, or Tn5 adapter sequences, complement bead adapter and Illumina® Handle sequences.

A hyperactive variant of the Tn5 transposase employed herein in the below Examples was derived from the naturally occurring wild-type Tn5 transposase. Three missense mutations in the 476 residues of the Tn5 protein have typically been introduced: E54K, M56A, L372P, to produce the hyperactive variant. The wild type Tn5 transposon also contains two near-identical insertion sequences (IS50L and IS50R) flanking three antibiotic resistance genes (Reznikoff 2008). Each IS50 contains two inverted 19-base pair end sequences. However, because wild-type end sequences exhibited relatively low activity, they were replaced in vitro by synthetic hyperactive mosaic end sequences. A complex of the hyperactive Tn5 transposase with the 19-base pair mosaic end sequences therefore can provoke the mutant Tn5 to induce DNA fragmentation.

Specific forms of DNA fragmenting agents/enzymes for use in the disclosure include, without limitation: transposases (including non-Tn5 transposases), DFF40, and DNases, including restriction endonucleases. In other embodiments of the disclosure, $H_2O_2$ (hydrogen peroxide) can be employed to fragment DNA.

Tagmentation

In certain aspects, the disclosure employs a Tn5 tagmentation reaction, in which a Tn5 enzyme randomly cleaves double stranded DNA into fragments and tags the DNA, by end-joining to the 5"-ends, synthetic adapter sequences. In one embodiment of the disclosure, the synthetic adapters, or Tn5 adapter sequences, are equivalent to the published Illumina® Nextera Transposase Adapters. In embodiments, "tagmentation" refers to sequencing techniques that employ a hyperactive mutant form of Tn5 enzyme as described above. The tagmentation results in the simultaneous fragmentation of the DNA and ligation of the adapter sequences to the 5' ends of both strands of duplex fragments. Following a purification step to remove the Tn5 enzyme or the hyperactive mutant form of the Tn5 enzyme, additional sequences can be added to the ends of the adapted fragments, for example by PCR, ligation, or any other suitable methodology known to those of skill in the art. Following sequencing using next-generation sequencing, the sequencing reads can then be used to infer regions of increased accessibility as well as to map regions of transcription factor binding sites and nucleosome positions. The number of reads for a region correlate with the degree of accessibility of the chromatin region.

The number of steps required to transform DNA into adapter sequence-modified templates in solution ready for cluster formation and sequencing can be minimized by the use of Tn5 transposase based tagmentation. Exemplary transposition procedures and systems that can be readily adapted for use with the transposases of the present disclosure are described, for example, in WO 10/048605; US Patent Publication No. 2012/0301925; US Patent Publication No. 2013/0143774, each of which is incorporated herein by reference in its entirety.

Amplification Techniques

A method as set forth herein can employ any of a variety of amplification techniques. Exemplary amplification techniques that can be used include, but are not limited to, polymerase chain reaction (PCR), rolling circle amplification (RCA), multiple displacement amplification (MDA), and random prime amplification (RPA). In some embodiments the amplification can be carried out in solution, for example, when features of an array are capable of containing amplicons in a volume having a desired capacity. Formats that utilize two species of primers are often referred to as bridge amplification because double stranded amplicons form a bridge-like structure between the two surface-attached primers that flank the template sequence that has been copied. Exemplary reagents and conditions that can be used for bridge amplification are described, for example, in U.S. Pat. Nos. 5,641,658; 7,115,400; and 8,895,249; and/or U.S. Patent Publication Nos. 2002/0055100 A1, 2004/0096853 A1, 2004/0002090 A1, 2007/0128624 A1 and 2008/0009420 A1, each of which is incorporated herein by reference. Solid-phase PCR amplification can also be carried out with one of the amplification primers and the second primer in solution. An exemplary format that uses a combination of a surface-attached primer and soluble primer is the format used in emulsion PCR as described, for example, in Dressman et al., Proc. Natl. Acad. Sci. USA 100:8817-8822 (2003), PCT Publication No. WO 05/010145, or U.S. Patent Publication Nos. 2005/0130173 or 2005/0064460, each of which is incorporated herein by reference. Emulsion PCR is illustrative of the format and it will be understood that for purposes of the methods set forth herein the use of an emulsion is optional and indeed for several embodiments an emulsion is not used.

RCA techniques can be modified for use in a method of the present disclosure. Exemplary components that can be used in an RCA reaction and principles by which RCA produces amplicons are described, for example, in Lizardi et al., Nat. Genet. 19:225-232 (1998) and U.S. Patent Publication No. 2007/0099208, each of which is incorporated herein by reference. Primers used for RCA can be in solution. The primers can be one or more of the universal primers described herein.

MDA techniques can be modified for use in a method of the present disclosure. Some basic principles and useful conditions for MDA are described, for example, in Dean et al., Proc Natl. Acad. Sci. USA 99:5261-66 (2002); Lage et al., Genome Research 13:294-307 (2003); Walker et al., Molecular Methods for Virus Detection, Academic Press, Inc., 1995; Walker et al., Nucl. Acids Res. 20:1691-96 (1992); U.S. Pat. Nos. 5,455,166; 5,130,238; and 6,214,587, each of which is incorporated herein by reference. Primers used for MDA can be in solution or attached to a bead or other solid support at an amplification site. Again, the primers can be one or more of the universal primers described herein.

In particular embodiments a combination of the above-exemplified amplification techniques can be used. For example, RCA and MDA can be used in a combination wherein RCA is used to generate a concatameric amplicon in solution (e.g., using solution-phase primers). The amplicon can then be used as a template for MDA using primers (e.g., universal primers).

Nucleic Acid Detection Techniques

Exemplary nucleic acid detection methods include, but are not limited to, nucleic acid sequencing of a probe, hybridization of nucleic acids to a probe, ligation of nucleic acids that are hybridized to a probe, extension of nucleic acids that are hybridized to a probe, extension of a first nucleic acid that is hybridized to a probe followed by ligation of the extended nucleic acid to a second nucleic acid that is hybridized to the probe, or other methods known in the art such as those set forth in U.S. Pat. No. 8,288,103 or 8,486,625, each of which is incorporated herein by reference.

Sequencing Techniques

In one embodiment of the present disclosure, the unblocked fragments are amplified and sequenced in bulk via a sequencing platform (e.g., Illumina® platform) which utilizes sequencing techniques, such as the sequencing-by-synthesis (SBS) technique. To initiate a first SBS cycle, one or more labeled nucleotides, DNA polymerase, SBS primers etc., can be contacted with one or more features (e.g., feature(s) where nucleic acid probes are attached). Those features where SBS primer extension causes a labeled nucleotide to be incorporated can be detected. Optionally, the nucleotides can include a reversible termination moiety that terminates further primer extension once a nucleotide has been added to the SBS primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the bead or other solid support (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with a composition, apparatus or method of the present disclosure are described, for example, in Bentley et al., Nature 456:53-59 (2008), PCT Publication Nos. WO 91/06678, WO 04/018497 or WO 07/123744; U.S. Pat. Nos. 7,057,026, 7,329,492, 7,211,414, 7,315,019 or 7,405,281, and U.S. Patent Publication No. 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 1 1 (1), 3-1 1 (2001); Ronaghi et al. Science 281 (5375), 363 (1998); or U.S. Pat. Nos. 6,210,891, 6,258,568 or 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system.

Excitation radiation sources used for fluorescence based detection systems are not necessary for pyrosequencing procedures. Useful fluidic systems, detectors and procedures that can be used for application of pyrosequencing to apparatus, compositions or methods of the present disclosure are described, for example, in PCT Patent Publication No. WO2012/058096, US Patent Publication No. 2005/0191698 A1, or U.S. Pat. Nos. 7,595,883 or 7,244,559, each of which is incorporated herein by reference.

Sequencing-by-ligation reactions are also useful including, for example, those described in Shendure et al. Science 309:1728-1732 (2005); or U.S. Pat. Nos. 5,599,675 or 5,750,341, each of which is incorporated herein by reference. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251 (4995), 767-773 (1995); or PCT Publication No. WO 1989/10977, each of which is incorporated herein by reference. In both sequencing-by-ligation and sequencing-by-hybridization procedures, target nucleic acids (or amplicons thereof) that are present at sites of an array are subjected to repeated cycles of oligonucleotide delivery and detection. Compositions, apparatus or methods set forth herein or in references cited herein can be readily adapted for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some sequencing embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zero-mode waveguides (ZMWs). Techniques and reagents for FRET-based sequencing are described, for example, in Levene et al. Science 299, 682-686 (2003); Lundquist et al. Opt. Lett. 33, 1026-1028 (2008); and Korlach et al. Proc. Natl. Acad. Sci. USA 105, 1 176-1 181 (2008), each of which is incorporated herein by reference.

Some sequencing embodiments include detection of a proton released upon incorporation of a nucleotide into an extension product. For example, sequencing based on detection of released protons can use an electrical detector and associated techniques that are commercially available from Ion Torrent (Guilford, C T, a Life Technologies and Thermo Fisher subsidiary) or sequencing methods and systems described in U.S. Patent Publication Nos. 2009/0026082 A1; 2009/0127589 A1; 2010/0137143 A1; or U.S. Publication No. 2010/0282617 A1, each of which is incorporated herein by reference.

A method of the present disclosure can include a step of contacting a biological specimen (i.e., a sectioned tissue sample treated with a permeabilizing agent and/or a DNA fragmenting agent and/or an agent for disrupting nucleosomes/histones or other cellular components that confer genomic/chromatin structure, thereby allowing for increased genomic accessibility while using the approach) light-activated nucleic acid probes attached thereto. The identity and location of the light-activated nucleic acid probes may have been decoded prior to contacting the biological specimen with the bead or other solid support.

A light-activated nucleic acid probe used in a composition or method set forth herein can include a target capture moiety. In particular embodiments, the target capture moiety is a target capture sequence. The target capture sequence is generally complementary to a target sequence such that target capture occurs by formation of a probe-target hybrid complex. A target capture sequence can be any of a variety of lengths.

In certain embodiments, a plurality of different nucleic acid probes can include different target capture sequences that hybridize to different target nucleic acid sequences from a biological specimen. Different target capture sequences can be used to selectively bind to one or more desired target nucleic acids from a biological specimen. In some cases, the different nucleic acid probes can include a target capture sequence that is common to all or a subset of the probes on a solid support. For example, the light activated nucleic acid probes can be complementary to a transposon adapter sequence, e.g., where tagmentation is performed. Such probes or amplicons thereof can hybridize to tagmented DNA molecules or amplicons thereof. Although target DNA insert sequences will differ, capture will be mediated by the common sequence regions complementary to transposon adapter sequences.

A method set forth herein can include a step of hybridizing light-activated nucleic acid probes to target nucleic acids that are from portions of the biological specimen that are proximal to the probes. Generally, a target nucleic acid will flow or diffuse from a region of the biological specimen to an area of the probe-presenting bead array that is in proximity with that region of the specimen. Here the target nucleic acid will interact with nucleic acid probes that are proximal to the region of the specimen from which the target nucleic acid was released. A target-probe hybrid complex can form where the target nucleic acid encounters a complementary target capture sequence on a nucleic acid probe. The location of the target-probe hybrid complex will generally correlate with the region of the biological specimen from where the target nucleic acid was derived. In certain embodiments, the plurality of light-activated nucleic acid probes with bind to the target nucleic acids on the biological specimen and a plurality of target-probe hybrids will be formed. The sequences of the target nucleic acids and their locations determined by tagmentation will provide spatial information about the nucleic acid content of the biological specimen.

An embodiment of the present disclosure may include a step of extending light-activated probes to which target nucleic acids are hybridized. The extended probes are thus spatially tagged versions of the target nucleic acids from the biological specimen. The sequences of the extended probes identify what nucleic acids are in the biological specimen and where in the biological specimen the target nucleic acids are located. It will be understood that other sequence elements that are present in the nucleic acid probes can also be included in the extended probes (see, e.g., description as provided elsewhere herein). Such elements include, for example, primer binding sites, cleavage sites, other tag sequences (e.g., sample identification tags), capture sequences, recognition sites for nucleic acid binding proteins or nucleic acid enzymes, or the like.

Extension of probes can be carried out using methods exemplified herein or otherwise known in the art for amplification of nucleic acids or sequencing of nucleic acids. In particular embodiments one or more nucleotides can be added to the 3' end of a nucleic acid, for example, via polymerase catalysis (e.g., DNA polymerase). Chemical or enzymatic methods can be used to add one or more nucleotide to the 3' or 5' end of a nucleic acid. One or more oligonucleotides can be added to the 3' or 5' end of a nucleic acid, for example, via chemical or enzymatic (e.g., ligase catalysis) methods. A nucleic acid can be extended in a template directed manner, whereby the product of extension is complementary to a template nucleic acid that is hybridized to the nucleic acid that is extended. Exemplary methods for extending nucleic acids are set forth in US Patent Publication No. US 2005/0037393 or U.S. Pat. No. 8,288, 103 or 8,486,625, each of which is incorporated herein by reference.

All or part of a target nucleic acid that is hybridized to a nucleic acid probe can be copied by extension. For example, an extended probe can include at least, 1, 2, 5, 10, 25, 50, 100, 200, 500, 1000 or more nucleotides that are copied from a target nucleic acid. The length of the extension product can be controlled, for example, using reversibly terminated nucleotides in the extension reaction and running a limited number of extension cycles. The cycles can be run as exemplified for SBS techniques and the use of labeled nucleotides is not necessary.

Accordingly, an extended probe produced in a method set forth herein can include no more than 1000, 500, 200, 100, 50, 25, 10, 5, 2 or 1 nucleotides that are copied from a target nucleic acid. Of course extended probes can be any length within or outside of the ranges set forth above.

It will be understood that light activated probes used in a method, composition or apparatus set forth herein need not be nucleic acids. Other molecules can be used such as proteins, carbohydrates, small molecules, particles or the like. Light activated probes can be a combination of a nucleic acid component (e.g., having a barcode, primer binding site, cleavage site and/or other sequence element set forth herein) and another moiety (e.g., a moiety that captures or modifies a target nucleic acid).

Exemplary cleavage sites include, but are not limited to, moieties that are susceptible to a chemical, enzymatic or physical process that results in bond breakage. For example, the location can be a nucleotide sequence that is recognized by an endonuclease. Suitable endonucleases and their recognition sequences are well known in the art and in many cases are even commercially available (e.g., from New England Biolabs, Beverley MA; ThermoFisher, Waltham, MA or Sigma Aldrich, St. Louis MO). A particularly useful endonuclease will break a bond in a nucleic acid strand at a site that is 3'-remote to its binding site in the nucleic acid, examples of which include Type II or Type IIs restriction endonucleases. In some embodiments an endonuclease will cut only one strand in a duplex nucleic acid (e.g., a nicking enzyme). Examples of endonucleases that cleave only one strand include Nt.BstNBI and Nt.AlwI.

In some embodiments, a cleavage site is an abasic site or a nucleotide that has a base that is susceptible to being removed to create an abasic site. Examples of nucleotides that are susceptible to being removed to form an abasic site include uracil and 8-oxo-guanine. Abasic sites can be created by hydrolysis of nucleotide residues using chemical or enzymatic reagents. Once formed, abasic sites may be cleaved (e.g., by treatment with an endonuclease or other single-stranded cleaving enzyme, exposure to heat or alkali), providing a means for site-specific cleavage of a nucleic acid. An abasic site may be created at a uracil nucleotide on one strand of a nucleic acid. The enzyme uracil DNA glycosylase (UDG) may be used to remove the uracil base, generating an abasic site on the strand. The nucleic acid strand that has the abasic site may then be cleaved at the abasic site by treatment with endonuclease (e.g., EndoIV endonuclease, AP lyase, FPG glycosylase/AP lyase, EndoVIII glycosylase/AP lyase), heat or alkali. In a particular embodiment, the USER™ reagent available from New England Biolabs is used for the creation of a single nucleotide gap at a uracil base in a nucleic acid.

Abasic sites may also be generated at non-natural/modified deoxyribonucleotides other than uracil and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g., EndoIV or AP lyase).

Other examples of cleavage sites and methods that can be used to cleave nucleic acids are set forth, for example, in U.S. Pat. No. 7,960,120, which is incorporated herein by reference.

The number of blocked adapters consisting of an oligonucleotide sequence can vary across a wide range, e.g., billions, or more. It is further expressly contemplated that in addition to the above-described sequence features, oligonucleotides of the disclosure can possess any number of other art-recognized features while remaining within the scope of the disclosure.

Tissue Samples and Sectioning

In some embodiments, a tissue section is employed. The tissue can be derived from a multicellular organism. Exemplary multicellular organisms include, but are not limited to a mammal, plant, algae, nematode, insect, fish, reptile, amphibian, fungi or *Plasmodium falciparum*. Exemplary species are set forth previously herein or known in the art. The tissue can be freshly excised from an organism or it may have been previously preserved for example by freezing, embedding in a material such as paraffin (e.g., formalin fixed paraffin embedded samples), formalin fixation, infiltration, dehydration or the like. Optionally, a tissue section can be cryosectioned, using techniques and compositions as described herein and as known in the art. As a further option, a tissue can be permeabilized and the cells of the tissue lysed. Any of a variety of art-recognized lysis treatments can be used. Target nucleic acids that are released from a tissue that is permeabilized can be captured by nucleic acid probes, as described herein and as known in the art.

A tissue can be prepared in any convenient or desired way for its use in a method, composition or apparatus herein. Fresh, frozen, fixed or unfixed tissues can be used. A tissue can be fixed or embedded using methods described herein or known in the art.

A tissue sample for use herein, can be fixed by deep freezing at temperature suitable to maintain or preserve the integrity of the tissue structure, e.g., less than −20° C. In another example, a tissue can be prepared using formalin-fixation and paraffin embedding (FFPE) methods which are known in the art. Other fixatives and/or embedding materials can be used as desired. A fixed or embedded tissue sample can be sectioned, i.e. thinly sliced, using known methods. For example, a tissue sample can be sectioned using a chilled microtome or cryostat, set at a temperature suitable to maintain both the structural integrity of the tissue sample and the chemical properties of the nucleic acids in the sample. Exemplary additional fixatives that are expressly contemplated include alcohol fixation (e.g., methanol fixation, ethanol fixation), glutaraldehyde fixation and paraformaldehyde fixation.

In some embodiments, a tissue sample will be treated to remove embedding material (e.g., to remove paraffin or formalin) from the sample prior to release, capture or modification of nucleic acids. This can be achieved by contacting the sample with an appropriate solvent (e.g., xylene and ethanol washes). Treatment can occur prior to contacting the tissue sample with a solid support-captured bead array as set forth herein or the treatment can occur while the tissue sample is on the solid support-captured bead array.

Exemplary methods for manipulating tissues for use with solid supports to which nucleic acids are attached are set forth in US Patent Publication No. 2014/0066318, which is incorporated herein by reference.

The thickness of a tissue sample or other biological specimen that is contacted with a bead array in a method, composition or apparatus set forth herein can be any suitable thickness desired. In representative embodiments, the thickness will be at least 0.1 µm, 0.25 µm, 0.5 µm, 0.75 µm, 1 µm, 5 µm, 10 µm, 50 µm, 100 µm or thicker. Alternatively or additionally, the thickness of a tissue sample that is contacted with bead array will be no more than 100 µm, 50 µm, 10 µm, 5 µm, 1 µm, 0.5 µm, 0.25 µm, 0.1 µm or thinner.

A particularly relevant source for a tissue sample is a human being. The sample can be derived from an organ, including for example, an organ of the central nervous system such as brain, brainstem, cerebellum, spinal cord, cranial nerve, or spinal nerve; an organ of the musculoskeletal system such as muscle, bone, tendon or ligament; an organ of the digestive system such as salivary gland, pharynx, esophagus, stomach, small intestine, large intestine, liver, gallbladder or pancreas; an organ of the respiratory system such as larynx, trachea, bronchi, lungs or diaphragm; an organ of the urinary system such as kidney, ureter, bladder or urethra; a reproductive organ such as ovary, fallopian tube, uterus, vagina, placenta, testicle, epididymis, vas deferens, seminal vesicle, prostate, penis or scrotum; an organ of the endocrine system such as pituitary gland, pineal gland, thyroid gland, parathyroid gland, or adrenal gland; an organ of the circulatory system such as heart, artery, vein or capillary; an organ of the lymphatic system such as lymphatic vessel, lymph node, bone marrow, thymus or spleen; a sensory organ such as eye, ear, nose, or tongue; or an organ of the integument such as skin, subcutaneous tissue or mammary gland. In some embodiments, a tissue sample is obtained from a bodily fluid or excreta such as blood, lymph, tears, sweat, saliva, semen, vaginal secretion, ear wax, fecal matter or urine.

A sample from a human can be considered (or suspected) healthy or diseased when used. In some cases, two samples can be used: a first being considered diseased and a second being considered as healthy (e.g., for use as a healthy control). Any of a variety of conditions can be evaluated, including but not limited to, cancer, an autoimmune disease, cystic fibrosis, aneuploidy, pathogenic infection, psychological condition, hepatitis, diabetes, sexually transmitted disease, heart disease, stroke, cardiovascular disease, multiple sclerosis or muscular dystrophy. Certain contemplated conditions include genetic conditions or conditions associated with pathogens having identifiable DNA abundance signatures.

Application of Wash Solution to Photolabile Sequencing Library (Optional)

In certain embodiments, a photolabile sequencing library is purified from the sample including a step of washing with a wash solution such as a buffered salt solution (or other stabilizing solution). Exemplified buffered salt solutions include saline-sodium citrate (SSC), for example at a NaCl concentration of about 0.2 M to 5 M NaCl, optionally at about 0.5 to 3 M NaCl, optionally at about 1 M NaCl. In addition to SSC, use of other types of buffered solutions is expressly contemplated, including, e.g., PBS, Tris buffered saline and/or Tris buffer, as well as, more broadly, any aqueous buffer possessing a pH between 4 and 10 and salt between 0-1 osmolarity.

Wash solutions can contain various additives, such as surfactants (e.g., detergents), enzymes (e.g., proteases and collagenases), cleavage reagents, or the like, to facilitate removal of the specimen. In some embodiments, the solid support is treated with a solution comprising a proteinase enzyme. Alternatively or additionally, the solution can include cellulase, hemicellulase or chitinase enzymes (e.g., if desiring to remove a tissue sample from a plant or fungal source). In some cases, the temperature of a wash solution will be at least 30° C., 35° C., 50° C., 60° C. or 90° C. Conditions can be selected for removal of a biological specimen while not denaturing hybrid complexes formed between target nucleic acids and attached light-activated nucleic acid probes.

Sequencing Methods

Some of the methods and compositions provided herein employ methods of sequencing nucleic acids. A number of DNA sequencing techniques are known in the art, including fluorescence-based sequencing methodologies (see e.g., Birren et al, Genome Analysis Analyzing DNA, 1, Cold Spring Harbor, N.Y., which is incorporated herein by reference in its entirety). In some embodiments, automated sequencing techniques understood in that art are utilized. In some embodiments, parallel sequencing of partitioned amplicons can be utilized (PCT Publication No. WO2006084132, which is incorporated herein by reference in its entirety). In some embodiments, DNA sequencing is achieved by parallel oligonucleotide extension (See, e.g., U.S. Pat. Nos. 5,750,341; 6,306,597, which are incorporated herein by reference in their entireties). Additional examples of sequencing techniques include the Church polony technology (Mitra et al, 2003, Analytical Biochemistry 320, 55-65; Shendure et al, 2005 Science 309, 1728-1732; U.S. Pat. Nos. 6,432,360, 6,485,944, 6,511,803, which are incorporated by reference), the 454 picotiter pyrosequencing technology (Margulies et al, 2005 Nature 437, 376-380; US 20050130173, which are incorporated herein by reference in their entireties), the Solexa single base addition technology (Bennett et al, 2005, Pharmacogenomics, 6, 373-382; U.S. Pat. Nos. 6,787,308; 6,833,246, which are incorporated herein by reference in their entireties), the Lynx massively parallel signature sequencing technology (Brenner et al. (2000). Nat. Biotechnol. 18:630-634; U.S. Pat. Nos. 5,695,934; 5,714,330, which are incorporated herein by reference in their entireties), and the Adessi PCR colony technology (Adessi et al. (2000). Nucleic Acid Res. 28, E87; WO 00018957, which are incorporated herein by reference in their entireties).

Next-generation sequencing (NGS) methods can be employed in certain aspects of the disclosure to obtain a high volume of sequence information (such as are particularly required to perform deep sequencing of bead-associated cellular DNAs following capture of such DNAs from treated tissue sections (e.g., treated cryosections)) in a highly efficient and cost effective manner. NGS methods share the common feature of massively parallel, high-throughput strategies, with the goal of lower costs in comparison to older sequencing methods (see, e.g., Voelkerding et al, Clinical Chem., 55: 641-658, 2009; MacLean et al, Nature Rev. Microbiol, 7-287-296; which are incorporated herein by reference in their entireties). NGS methods can be broadly divided into those that typically use template amplification and those that do not. Amplification-utilizing methods include pyrosequencing commercialized by Roche as the 454 technology platforms (e.g., GS 20 and GS FLX), the Solexa platform commercialized by Illumina®, and the Supported Oligonucleotide Ligation and Detection (SOLiD™) platform commercialized by Applied Biosystems. Non-amplification approaches, also known as single-molecule sequencing, are exemplified by the HeliScope platform commercialized by Helicos Biosciences, SMRT sequencing commercialized by Pacific Biosciences, and emerging platforms marketed by VisiGen and Oxford Nanopore Technologies Ltd.

In pyrosequencing (U.S. Pat. Nos. 6,210,891; 6,258,568, which are incorporated herein by reference in their entireties), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and 10 6 sequence reads can be achieved, resulting in up to 500 million base pairs (Mb) of sequence.

In the Solexa/Illumina® platform (Voelkerding et al, Clinical Chem., 55-641-658, 2009; MacLean et al, Nature Rev. Microbiol, 7:287-296; U.S. Pat. Nos. 6,833,246; 7,115, 400; 6,969,488, which are incorporated herein by reference in their entireties), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluorophore and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al, Clinical Chem., 55: 641-658, 2009; U.S. Pat. Nos. 5,912,148; and 6,130,073, which are incorporated herein by reference in their entireties) can initially involve fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (see, e.g., Astier et al, J. Am. Chem. Soc. 2006 Feb. 8; 128(5): 1705-10, which is incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore (or as individual nucleotides pass through the nanopore in the case of exonuclease-based techniques), this causes a change in the magnitude of the current through the nanopore that is distinct for each of the four bases, thereby allowing the sequence of the DNA molecule to be determined.

The Ion Torrent technology is a method of DNA sequencing based on the detection of hydrogen ions that are released during the polymerization of DNA (see, e.g., Science 327 (5970): 1190 (2010); U.S. Patent Publication Nos. 20090026082, 20090127589, 20100301398, 20100197507, 20100188073, and 20100137143, which are incorporated herein by reference in their entireties). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is approximately 99.6% for 50 base reads, with approximately 100 Mb generated per run. The read-length is 100 base pairs. The accuracy for homopolymer repeats of 5 repeats in length is approximately 98%. The benefits of ion semiconductor sequencing are rapid sequencing speed and low upfront and operating costs.

Imaging/Image Assembly

With the capture of targeted doubt-stranded DNA sequences from spatially-defined regions with diffraction-limited resolution, those DNAs captured by light activated probes containing oligonucleotides (capture probes) can be identified and high-resolution images that localize sites of DNA abundance can be readily constructed in silico. In certain embodiments of the present disclosure, targeted double-stranded DNA sequences can first be assigned to an image location, with all associated DNA sequence data also assigned to that position. High resolution images representing the extent of capture of individual or grouped DNAs across the various spatial positions can then be generated using the underlying DNA sequence information. Images (i.e., pixel coloring and/or intensities) can be adjusted and/or normalized using any (or any number of) art-recognized technique(s) deemed appropriate by one of ordinary skill in the art.

In certain embodiments, a high-resolution image of the disclosure is an image in which discrete features (e.g., pixels) of the image are spaced at 100 µm or less. In some embodiments, the spacing of discrete features within the image is at 50 µm or less, optionally 40 µm or less, optionally 30 µm or less, optionally 20 µm or less, optionally 15 µm or less, optionally 10 µm or less, optionally 9 µm or less, optionally 8 µm or less, optionally 7 µm or less, optionally 6 µm or less, optionally 5 µm or less, optionally 4 µm or less, optionally 3 µm or less, optionally 2 µm or less, or optionally 1 µm or less.

Images can be obtained using detection devices known in the art. Examples include microscopes configured for light, bright field, dark field, phase contrast, fluorescence, reflection, interference, or confocal imaging. A biological specimen can be stained prior to imaging to provide contrast between different regions or cells. In some embodiments, more than one stain can be used to image different aspects of the specimen (e.g., different regions of a tissue, different cells, specific subcellular components or the like). In other embodiments, a biological specimen can be imaged without staining.

In particular embodiments, a fluorescence microscope (e.g., a confocal fluorescent microscope) can be used to detect a biological specimen that is fluorescent, for example, by virtue of a fluorescent label. Fluorescent specimens can also be imaged using a nucleic acid sequencing device having optics for fluorescent detection such as a Genome Analyzer®, MiSeq®, NextSeq® or HiSeq® platform device commercialized by Illumina, Inc. (San Diego, CA); or a SOLiD™ sequencing platform commercialized by Life Technologies (Carlsbad, CA). Other imaging optics that can be used include those that are found in the detection devices described in Bentley et al., Nature 456:53-59 (2008), PCT Publication Nos. WO 91/06678, WO 04/018497 or WO 07/123744; U.S. Pat. Nos. 7,057,026, 7,329,492, 7,211,414, 7,315,019 or 7,405,281, and US Patent Publication No. 2008/0108082, each of which is incorporated herein by reference.

An image of a biological specimen can be obtained at a desired resolution, for example, to distinguish tissues, cells or subcellular components. Accordingly, the resolution can be sufficient to distinguish components of a biological specimen that are separated by at least 0.5 µm, 1 µm, 5 µm, 10 µm, 50 µm, 100 µm, 500 µm, 1 mm or more. Alternatively or additionally, the resolution can be set to distinguish components of a biological specimen that are separated by at least 1 mm, 500 µm, 100 µm, 50 µm, 10 µm, 5 µm, 1 µm, 0.5 µm or less.

A method set forth herein can include a step of correlating locations in an image of a biological specimen with light-activated nucleic acid probes to which the biological specimen is, was or will be contacted. Accordingly, characteristics of the biological specimen that are identifiable in the image can be correlated with the nucleic acids that are found to be present in their proximity. Any of a variety of morphological characteristics can be used in such a correlation, including for example, cell shape, cell size, tissue shape, staining patterns, presence of particular proteins (e.g., as detected by immunohistochemical stains) or other characteristics that are routinely evaluated in pathology or research applications. Accordingly, the biological state of a tissue or its components as determined by visual observation can be correlated with molecular biological characteristics as determined by spatially resolved nucleic acid analysis.

A solid support upon which a biological specimen is imaged can include fiducial markers to facilitate determination of the orientation of the specimen or the image thereof in relation to probes that are attached to the solid support. Exemplary fiducials include, but are not limited to, beads (with or without fluorescent moieties or moieties such as nucleic acids to which labeled probes can be bound), fluorescent molecules attached at known or determinable features, or structures that combine morphological shapes with fluorescent moieties. Exemplary fiducials are set forth in US Patent Publication No. 2002/0150909 A1 or U.S. patent application Ser. No. 14/530,299, each of which is incorporated herein by reference. One or more fiducials are preferably visible while obtaining an image of a biological specimen. The fiducials can be provided in a pattern, for example, along an outer edge of a perimeter of a location where a biological specimen resides. In one embodiment, one or more fiducials are detected using the same imaging conditions used to visualize a biological specimen. However, if desired separate images can be obtained (e.g., one image of the biological specimen and another image of the fiducials) and the images can be aligned to each other.

Kits

The disclosure also provides kits containing agents of this disclosure for use in the methods of the present disclosure. Kits of the disclosure may include one or more containers comprising an agent (e.g., permeabilizing agent) and/or composition (e.g., Tn5 transposase loaded with customized amplification-blocked adapters) of this disclosure. In some embodiments, the kits further include instructions for use in accordance with the methods of this disclosure. In some embodiments, these instructions comprise a description of administration of the agent to diagnose, e.g., a disease and/or malignancy. In some embodiments, the instructions comprise a description of how to create a tissue cryosection, treat a tissue section with a permeabilizing agent and/or a DNA fragmenting agent, form a spatially-defined (or simply spatially definable, pending performance of a step that defines the spatial resolution of the bead array) bead array, contact a tissue cryosection with a spatially-defined bead array and/or obtain captured, tissue cryosection-derived DNA sequence from the spatially-defined bead array. The kit may further comprise a description of selecting an individual suitable for treatment based on identifying whether that subject has a certain pattern of DNA abundance of one or more sequences in a cryosection sample.

Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for staging a cryosection and/or diagnosing a specific DNA abundance pattern in a cryosection. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. The container may further comprise a pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J.

Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Photoselective Sequencing Provides Spatially Targeted Sequence Data

The techniques herein provide photoselective sequencing, a sequencing methodology that enables non-invasive targeted genomic and epigenomic sequencing of spatially-defined cellular or subcellular regions of tissues or cell populations or cells using light-activated probes. In particular, the disclosure provides in-situ tagmentation with blocked adapters consisting of an oligonucleotide sequence conjugated to a fluorophore via a photocleavable spacer. Photo-induced cleavage of the spacer removes the fluorophore and uncages a 5' phosphate group that enables ligation of secondary adapters, which are subsequently used to amplify the selected DNA fragments after digestion of the sample. Advantageously, photoselective sequencing provides diffraction-limited resolution and straightforward compatibility with varied genomic and epigenetic sequencing libraries. Additionally, photoselective sequencing is not limited to spatially localized populations of cells.

As shown in FIG. 1, photoselective sequencing may involve: step 100 obtaining the tissue or cell sample from a subject; step 200 fixing the tissue or cell sample with a fixing agent; step 300 staining the fixed tissue or cell sample; step 400 preparing a photolabile sequencing library using a DNA fragmenting agent loaded with amplification-blocked adapters; step 500 targeting illumination of the fixed tissue or cell sample with near-UV light to unblock the adapters in a region of interest; step 600 purifying DNA from the sample; and step 700 amplifying and sequencing the unblocked adapters on a sequencing platform.

Figure 2A:
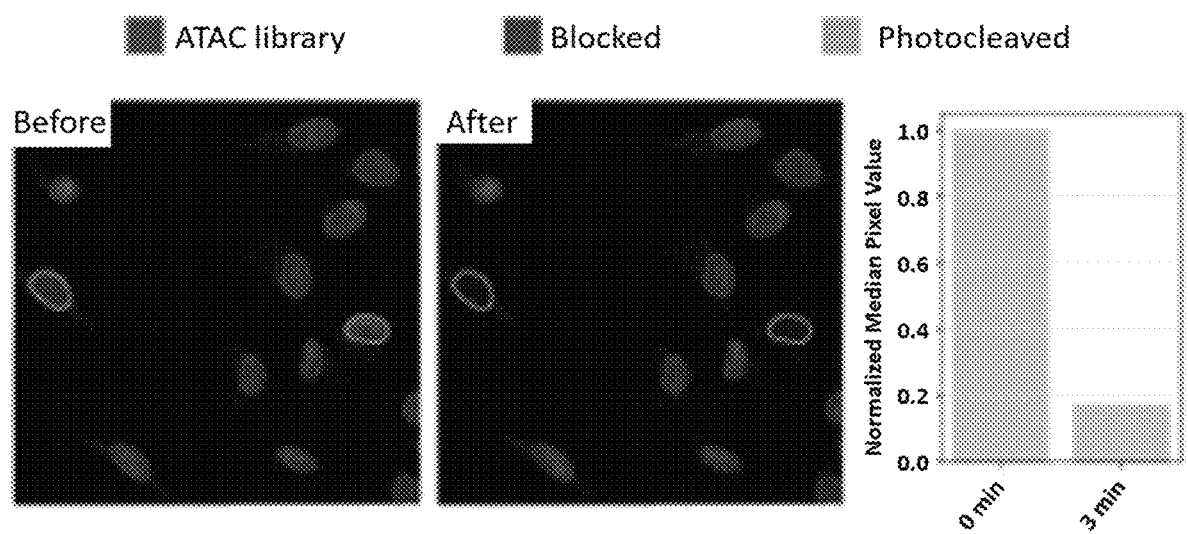
FIGS. 2A-2E depict an image, a graph, a bar graph, two images, and a scatterplot, respectively.
Figure 2B:
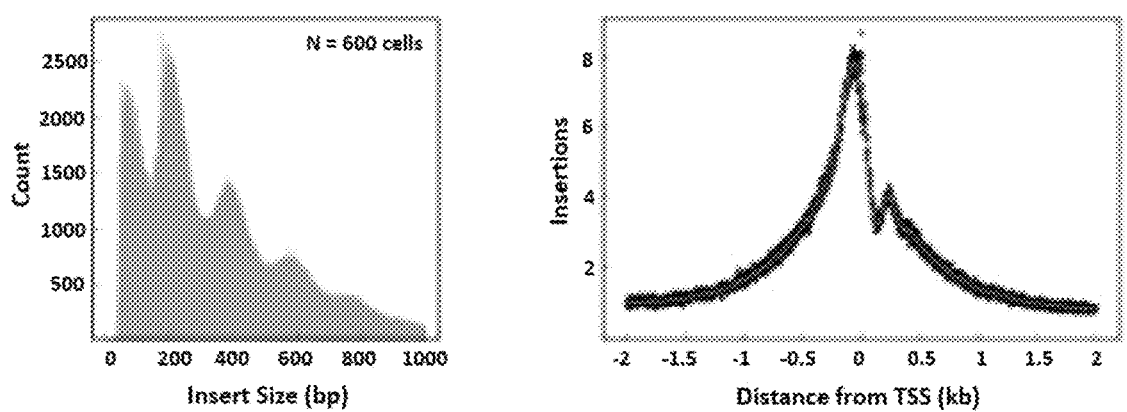

Preliminary data show that the amplification-blocked libraries can be successfully prepared in situ. For example, FIG. 2A shows an ATAC library prepared for photoselective sequencing in HeLa cells. Successful cleavage of the amplification-block in targeted cells (see e.g., yellow outline) removes the fluorophore and unblocks the library, as indicated by a loss of fluorescence. Libraries prepared for photoselective sequencing display hallmark properties of the established versions of the corresponding library preparations. For example, sequenced ATAC libraries in HeLa cells (prepared according to the photoselective sequencing protocol described herein) show high enrichment in transcription-start-sites, and a periodic fragment size distribution as expected (see e.g., FIG. 2B).

Figure 2C:
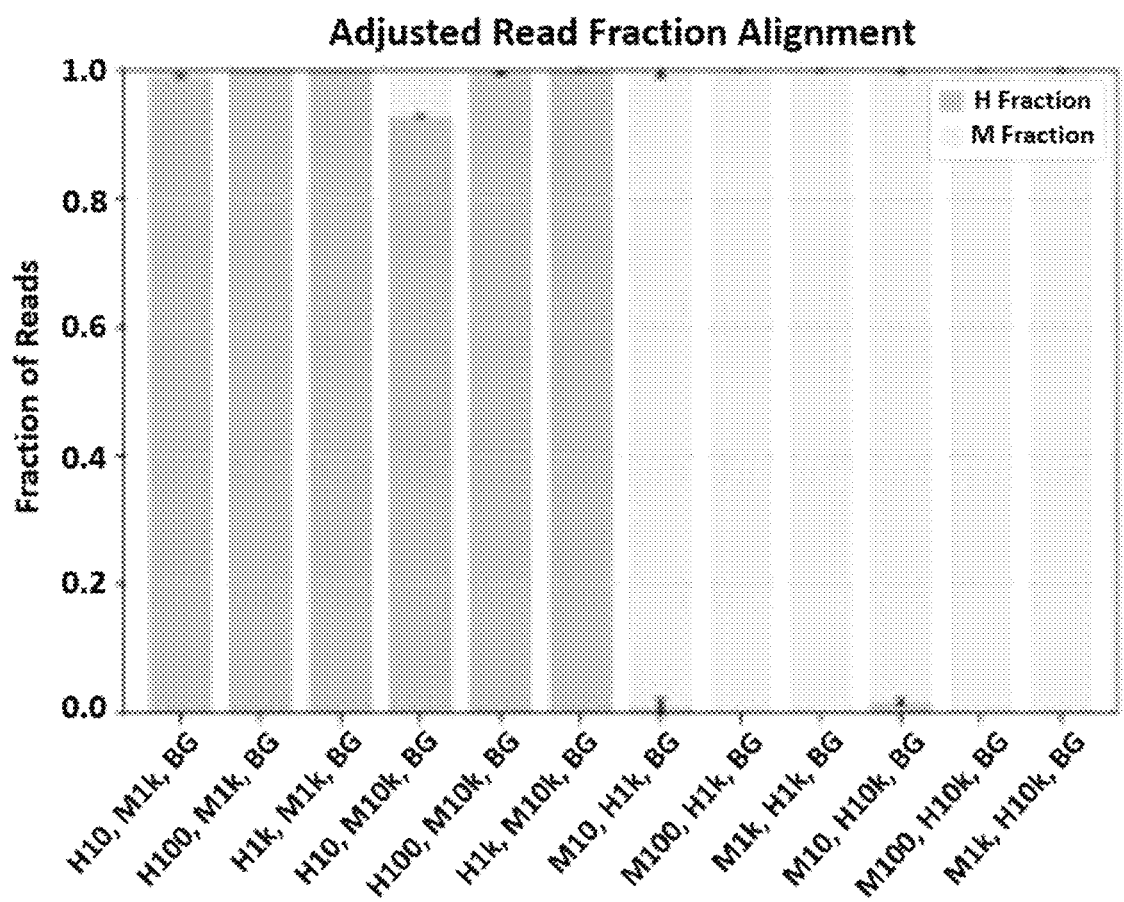

Photoselective sequencing has a low level of background fragments (e.g., fragments that were not intentionally unblocked), as indicated by a species mixing experiment. Tagmented DNA from various numbers of human and mouse cells was mixed, however, only fragments from only one of the two species were unblocked using the photoselective sequencing mechanism. The photoselective sequencing library preparation was carried out on the mixed-DNA sample and the number of human and mouse reads were quantified by sequencing an alignment to the respective genomes. The results (see e.g., FIG. 2C) show that, for example, even when the unblocked DNA-fragments from 10 human cells is mixed with blocked DNA from 10,000 mouse cells, the vast majority of reads (>90%) align to the human genome.

Figure 2D:
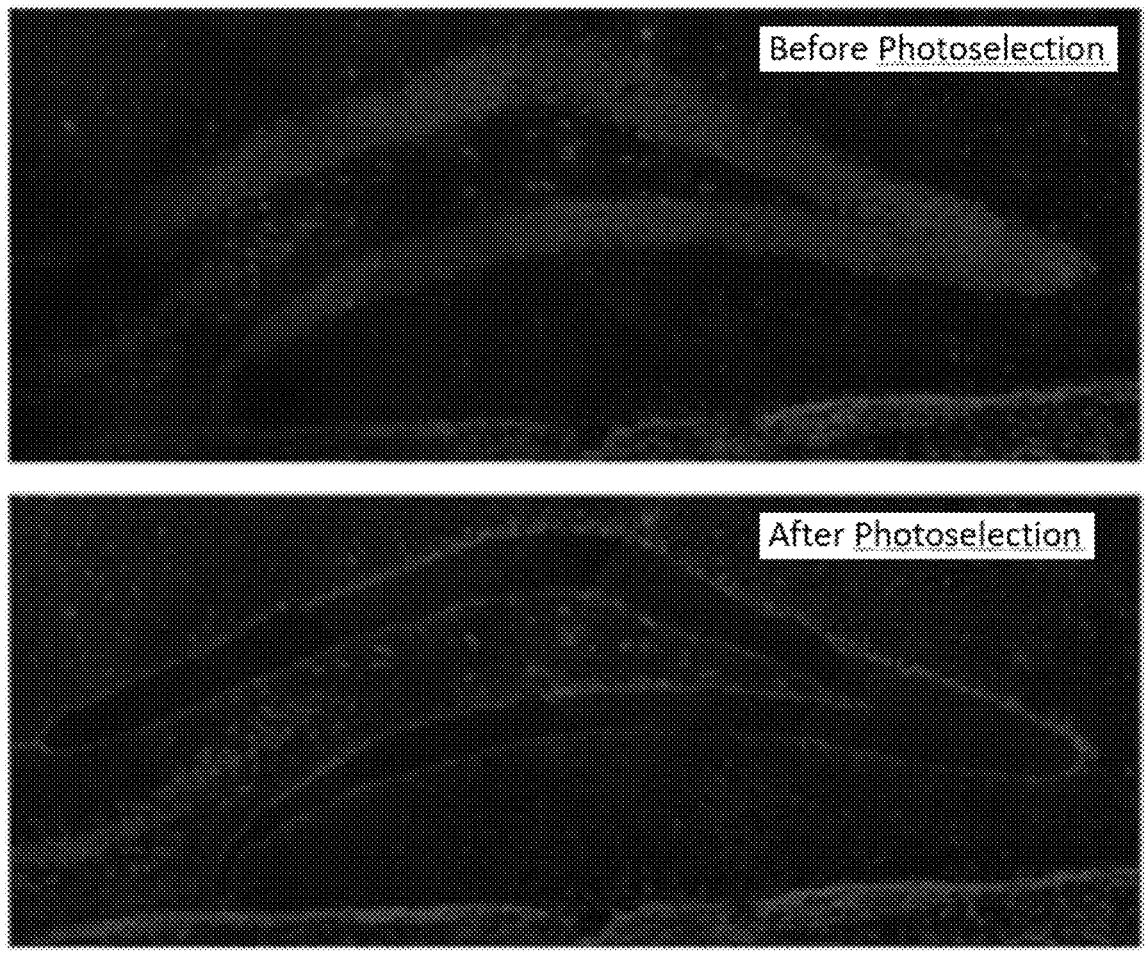
Figure 2E:
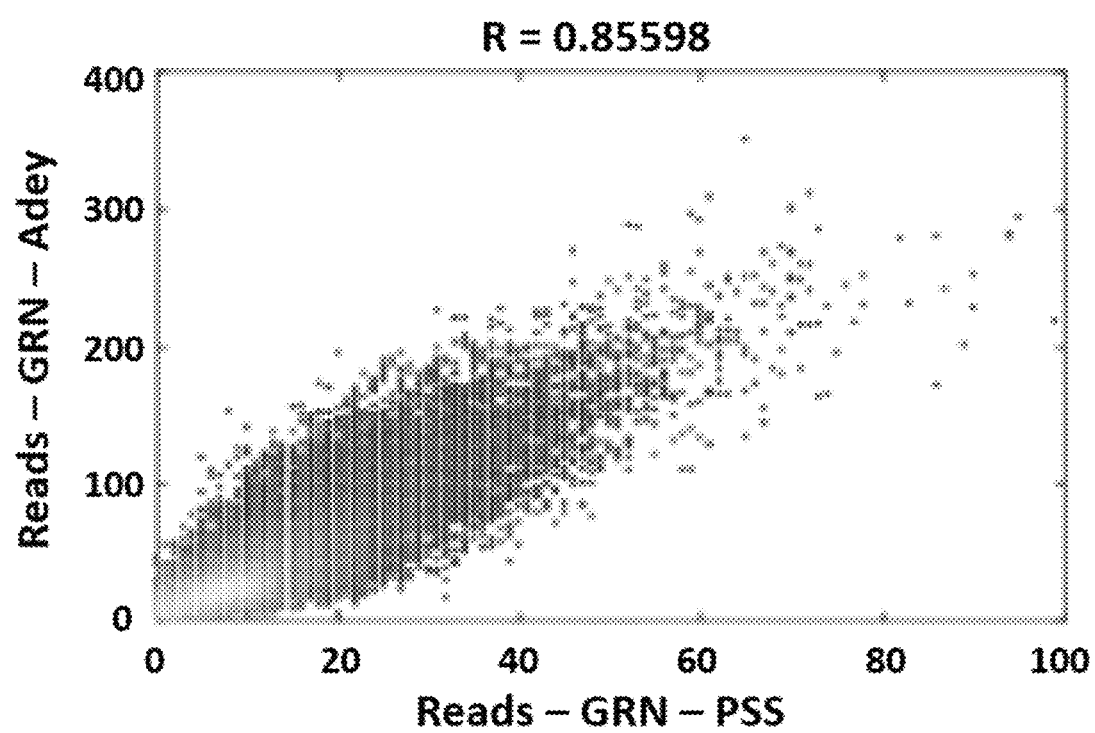

Furthermore, photoselective sequencing recapitulates data derived from single-cell ATAC. A photoselective ATAC library was prepared in sections from the hippocampal region of a wild type mouse brain, and the dentate dentate gyrus region was selected by exposure to 405 nm light (see e.g., FIG. 2D). The sequencing reads from the photoselected libraries were aligned to the mouse genome and compared to granule cell data from a reference single-cell ATAC data set (where granule cells were called computationally) obtained from Sinnamon et al. (Genome Res. 2019 May; 29(5):857-869). A feature set was created by pooling the photoselective sequencing reads with the published sequencing reads, and calling peaks on the joint data set. To compare the data two sets, the fraction of reads lying in each peak was compared between the data sets (see e.g., FIG. 2E) establishing high correlation between the data produced by the two methods (correlation coefficient ~0.86).

Example 2: Materials and Methods

Sample Protocol for Photoselective Sequencing in Cells and Tissues:

Unless otherwise specified all steps are carried out at room temperature in a volume of solution that is large enough to completely cover the sample.

Sample Preparation:

Adherent cells are cultured in an appropriate growth medium and split onto an imaging-compatible dish or slide. For tissues, 10 uM sections of a fresh-frozen sample are collected and placed onto a glass-bottom imaging dish or microscope slide. The tissue is lightly melted onto the glass by touching the underlying glass briefly with one finger.

Fixation and Permeabilization (Cells):

Cells are rinsed once in 1×PBS, then lightly fixed for 10 minutes at room temperature in 0.4% paraformaldehyde (PFA). Excess PFA is removed from the sample by washing 3 times for 5 minutes each with 1×PBS. Next, cells are permeabilized by incubating in 0.5% Triton X-100 in 1×PBS for 10 minutes at room temperature. The sample is again washed three times for 5 minutes each in 1×PBS.

Fixation and Permeabilization (Tissues):

Tissue slices are incubated in 1% PFA for 10 minutes at room temperature. The fixation reaction is quenched by the addition of 250 mM Tris pH 8 for 5 minutes. The sample is washed 2×5 min in 1×PBS, then incubated in 0.5% Triton X-100 in 1×PBS for 20 minutes at room temperature, then washed another 3×5 min in 1×PBS Staining for Regions of Interest:

At this point the sample is stained for cells or subcellular regions of interest using standard protocols. This may include immunofluorescence against proteins that mark subcellular regions or cell types of interest, a DAPI stain to identify cellular regions based on morphology, or FISH targeting cell-specific gene markers, or particular chromosomes. For example, in immunofluorescence, the sample is blocked for 30 minutes at room temperature in 4% bovine serum albumin dissolved in 0.1% PBSTween (1×PBS containing 0.1% Tween 20). The sample is next stained with a 1:200 dilution of the primary antibody, either at room temperature for 1 hour or overnight at 4° C. Excess primary antibody is removed by washing 3×5 minutes with 0.1% PBSTween. The sample is then stained with a fluorescently-labeled secondary antibody for 1 hour at room temperature, then washed 3×5 minutes with 1×PBS.

Annealing Adapters:

Tagmentation adapters (Adapter 1 and Adapter 2) are annealed to the mosaic end sequence by mixing 12.25 µL of 100 uM Adapter 1, 12.25 µL of 100 µM Adapter 2, 24 µL of 100 uM Mosaic End, 0.5 µL of 1 M Tris, pH 8, and 0.5 µL of 5 M NaCl in a PCR strip tube. The mixture is heated to 85° C. and cooled to 20° C. over the course of 1-1.5 hours. The annealed oligos are mixed with 50 uL of 100% glycerol and stored at −20° C. until loaded into the Tn5 transposase.

Loading Tn5 Transposase:

Tn5 is loaded by combining 13.5 µM Tn5 transposase with annealed oligos and dilution buffer (50% glycerol, 50 mM Tris pH 7.5, 100 mM NaCl, 100 µM EDTA, 1 mM DTT, 0.1% NP-40) in a 1:2:1 ratio. The mixture is incubated for 30 min at room temperature, then transferred to −20° C. for storage up to one week, or used immediately for tagmentation.

Modifications to Tagmentation Reaction:

If whole genome sequencing is desired, the sample is treated with 0.1N HCl for 5 min at room temperature to denature histones and allow uninform tagmentation. Protein targeted tagmentation can be achieved by specifically tethering the loaded Tn5 to the protein of interest, typically through the use of a ProteinA-Tn5 transposase fusion which will bind an antibody stain. Proceeding without modifications at this point will result in an ATAC library.

Tagmentation:

Loaded Tn5 transposase is either diluted 1/20 (cells) or 2/5 (tissues) in reaction buffer (in 0.3×PBS, 10 mM Tris pH 8.5, 5 mM $MgCl_2$). The mixture is incubated at 37° C. for 3 hours in a humidified incubator. The tagmentation reaction is quenched by rinsing the sample once with 50 mM EDTA in 1×PBS, then incubating for an additional 30 minutes at 37° C. in fresh 50 mM EDTA in 1×PBS.

Photoselection:

The sample is visualized by light microscopy to identify regions of interest that will be targeted for sequencing. The tagmented DNA in these regions of interest are unblocked by exposure to a focused beam of near-ultraviolet light (e.g., a 405 nm laser line focused onto the sample plane). This can be accomplished using a laser-scanning confocal microscope, a commercially available targeted illumination device, or a custom setup. To ensure that the library is fully unblocked in regions of interest the fluorescence of the library is monitored by visualizing the fluorophore at the 5' ends of the tagmentation adapters (e.g. Alexa Fluor 546) during photocleavage. Targeted illumination continues until there is at least an 80% reduction of fluorescence from the library in the targeted regions, indicating sufficient removal of the block.

Purification of Libraries:

After photoselection, the sample is digested by incubating the sample overnight at 55° C. with Proteinase K diluted 1:50 in a buffer containing 50 mM Tris pH 8, 50 mM NaCl and 0.4% SDS. The digested samples are column purified and eluted in 10 mM Tris pH 8. This recovers a mixture of blocked and unblocked fragments; however, only unblocked fragments will be ligated in subsequent steps.

Ligation of Secondary Adapters:

Secondary adapters are (P5 ligation adapter, P7 ligation adapter) are hybridized to the tagmented DNA using splints (Adapter 1 splint and Adapter 2 splint) that bridge the tagmentation and secondary adapters. To do this the photo-selected DNA is combined with 1 µM P5 ligation adapter, 1 µM P7 ligation adapter, 1 µM Adapter 1 splint, 1 µM Adapter 2 splint in 1×T4 DNA ligase buffer (NEB). The mixture is heated to 68° C. and cooled −0.1° C./s until it reaches 22° C. T4 DNA ligase (NEB) is then spiked into the reaction (1 µL ligase/10 µL total reaction volume), and the ligation reaction is incubated for 30 minutes at 22° C. The ligation reaction is cleaned using 1.8×AMPureXP beads (Beckman Coulter) according to the manufactures directions and eluted in 10 mM Tris pH 8.

Amplification of Libraries:

Cleaned ligation reactions are amplified for sequencing using NEBNext PCR master mix with primers PCR 1 and PCR 2, both at 1.25 µM. The thermocycling conditions are as follows: 5 min at 72° C., 30 s at 90° C., 5 repeats of 10s at 98° C. then 1 min 30s at 72° C., 2 min at 72° C., hold at 4° C. After an initial 5 cycles of PCR, the additional number of cycles needed is determined by performing qPCR on 10 µL of the previously amplified DNA. The qPCR reaction uses the same components as the initial PCR, except with the addition of SYBR green at a final concentration of 1×. The additional number of cycles taken as the number of cycles required to reach ¼ to ½ saturation as determined by qPCR. These additional cycles are applied to the remainder of the previously amplified DNA. Following additional rounds of PCR the samples are cleaned using 1.8×AMPureXP (Beckman Coulter) according to the manufactures directions and eluted in ultrapure water (Invitrogen). The libraries are quantified using a Kapa Quantification Kit (Roche) as per the manufacturer's directions. Libraries are diluted and then sequenced on an Illumina platform as directed by the manufacturer.

Processing Sequencing Reads:

Any remaining adapter sequences are trimmed from the reads using a custom python script. Trimmed reads are aligned to an appropriate genome using Bowtie2. Duplicate reads are removed using Picard, resulting in filtered BAM files that can be used for downstream analysis as desired.

| Oligo | Sequence (5'-3') | SEQ ID NO: |
|---|---|---|
| Adapter 1 | /5Alex546N//iSpPC/TCGTCGGCAGCGTCAGATGTGTATAAGAGACAG | 1 |
| Adapter 2 | /5Alex546N//iSpPC/GTCTCGTGGGCTCGGAGATGTGTATAAGAGACAG | 2 |
| P5 ligation adapter | AATGATACGGCGACCACCGAGATCTACACCTCTCTAT | 4 |
| P7 ligation adapter | CAAGCAGAAGACGGCATACGAGATNNNNNNNNNCGACTCT | 5 |
| Adapter 1 spline | TGCCGACGAATAGAGAGGTGTAG/3ddC/ | 6 |
| Adapter 2 splint | CCCACGAGACAGAGTCAGTCG/3ddC/ | 7 |
| Mosiac end | /5phos/C*T*G*T*C*T*C*T*T*A*T*A*C*A*C*A*/3ddC/ | 8 |
| PCR 1 | AATGATACGGCGACCACCGAGATCTACAC | 9 |
| PCR 2 | CAAGCAGAAGACGGCATACGAGAT | 10 |

Table of oligos used in example protocol, written as they would be purchased from Integrated DNA Technologies (IDT™). /iSpPC/ is a photocleavable spacer, /5 Alex546N/ is a 5' Alexa Fluor 546 modification. The N bases in the P7 ligation adapter represent an index sequence that uniquely identifies each sample. /3ddC/ is a 3' dideoxycytidine modification that prevents extension by polymerases. /5phos/ is a 5' phosphate modification and * is a phosphorothiolate (or alternatively a phosphorothioate) bond.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The present disclosure teaches one skilled in the art to test various combinations and/or substitutions of chemical modifications described herein toward generating conjugates possessing improved contrast, diagnostic and/or imaging activity. Therefore, the specific embodiments described herein are not limiting and one skilled in the art can readily appreciate that specific combinations of the modifications described herein can be tested without undue experimentation toward identifying conjugates possessing improved contrast, diagnostic and/or imaging activity.

The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A method for obtaining targeted genomic and epigenomic sequence data from a tissue or cell sample, comprising:
    (i) obtaining the tissue or cell sample from a subject;
    (ii) fixing the tissue or cell sample with a fixing agent;
    (iii) staining the fixed tissue or cell sample;
    (iv) preparing a photolabile sequencing library using a DNA fragmenting agent loaded with amplification-blocked primary adapters, wherein the amplification-blocked primary adapters comprise an oligonucleotide sequence conjugated to a fluorophore via a photocleavable spacer;
    (v) targeting illumination of the fixed tissue or cell sample with near-UV light to unblock the primary adapters in a region of interest, wherein the unblocking of the primary adapters produces an exposed 5'phosphate on the primary adapter;
    (vi) contacting the exposed 5'phosphate with a secondary adapter under conditions sufficient to allow for ligation of the secondary adapter to the exposed 5'phosphate of the primary adapter and purifying DNA from the sample, or purifying DNA from the sample and contacting the exposed 5'phosphate with a secondary adapter under conditions sufficient to allow for ligation of the secondary adapter to the exposed 5'phosphate of the primary adapter; and
    (vii) amplifying and sequencing the secondary adapters on a sequencing platform.

2. The method of claim 1, further comprising the step of: permeabilizing the fixed tissue or cell sample of step (ii) with a permeabilizing agent.

3. The method of claim 2, wherein the permeabilizing agent is about 0.1% to about 0.5% surfactant, optionally wherein contacting of a section of the tissue sample with the surfactant is performed for a duration of time between about 10 minutes and about 60 minutes.

4. The method of claim 1, wherein the photocleavable spacer comprises a 10 atom long molecule which is cleaved upon absorption of near-ultraviolet light to produce the exposed 5'phosphate.

5. The method of claim 1, wherein the fixed tissue or cell sample of step (ii) is contacted with a permeabilizing agent, optionally wherein the permeabilizing agent is a surfactant at a concentration between about 0.01% and about 5%.

6. The method of claim 5, wherein the permeabilizing agent is selected from the group consisting of a surfactant, NP-40, methanol, acetone, Polysorbate 20, saponin, an accessory reagent, and digitonin.

7. The method of claim 5, wherein contacting a section of the tissue sample with a permeabilizing agent is performed for a duration of time between about 0.1 minute and about 30 minutes, optionally wherein the DNA fragmenting agent comprises a Tn5 transposase enzyme, optionally wherein the Tn5 transposase enzyme is present in a tagmentation buffer comprising the primary adapter and mosaic oligonucleotides.

8. The method of claim 1, wherein the DNA fragmenting agent is selected from the group consisting of a transposase; $H_2O_2$; sonication; and a DNase, optionally wherein the Dnase is a restriction endonuclease, optionally wherein a Tn5 enzyme in a tagmentation buffer comprising the primary adapter and mosaic oligonucleotides contacts a sectioned tissue sample for about 20 minutes to about 16 hours, optionally wherein the Tn5 enzyme in the tagmentation buffer comprising the primary adapter and mosaic oligonucleotides contacts the sectioned tissue sample at between about 25° C. and about 55° C.

9. The method of claim 1, wherein a section of the tissue sample is a fixed section or a cryosection.

10. The method of claim 1, wherein target DNA molecules for obtaining the targeted genomic and epigenomic sequence data are selected from the group consisting of genomic DNA molecules, mitochondrial DNA (mtDNA) molecules, viral DNA molecules (optionally retroviral DNA molecules or AAV DNA molecules) and bacterial DNA molecules.

11. The method of claim 1, wherein target DNA molecules for obtaining the targeted genomic and epigenomic sequence data are genomic DNA molecules, optionally wherein the genomic DNA molecules are enriched for accessible chromatin sequences, as compared to inaccessible chromatin sequences.

12. The method of claim 1, wherein the tissue sample is obtained from a tissue selected from the group consisting of brain, lung, liver, kidney, pancreas, heart, and gastrointestinal (GI) tract.

13. The method of claim 1, wherein the tissue sample is obtained from a tumor.

14. The method of claim 1, wherein the subject is a mammal, optionally a human.

15. The method of claim 1, wherein the sequencing platform is a Next Generation Sequencing (NGS) platform.

16. The method of claim 1, wherein:
the method comprises performing an established Tn5-transposase based library preparation, the Tn5-transposase based library preparation optionally comprising performing ATAC-seq, Cut & Tag, or whole-genome sequencing; and/or
the method further comprises step (x) generating an image of the tissue sample that depicts the location(s) and relative abundance of one or more captured target DNAs within the sample, optionally wherein the image is a two-dimensional image.

17. A method for non-invasive targeted genomic and epigenomic sequencing of spatially-defined cellular or subcellular region using light activated probes, comprising:
(i) obtaining cells or a tissue sample from a subject;
(ii) fixing and permeabilizing the cells or the tissue sample with a fixing agent and a permeabilizing agent;
(iii) staining the fixed cells or tissue sample to visualize one or more regions of interest by microscopy;
(iv) preparing a photolabile sequencing library using Tn5 transposase enzyme loaded with amplification-blocked primary adapters, wherein the primary adapters include an oligonucleotide sequence conjugated to a fluorophore via a photocleavable spacer;
(v) targeting illumination of the fixed cells or tissue sample with near-UV light to unblock the primary adapters in the one or more regions of interest, wherein the unblocking of the primary adapters produces an exposed 5'phosphate on the primary adapter;
(vi) contacting the exposed 5'phosphate with a secondary adapter under conditions sufficient to allow for ligation of the secondary adapter to the exposed 5'phosphate of the primary adapter and purifying DNA from the sample, or purifying DNA from the sample and contacting the exposed 5'phosphate with a secondary adapter under conditions sufficient to allow for ligation of the secondary adapter to the exposed 5'phosphate of the primary adapter; and
(vii) amplifying and sequencing the secondary adapters on a sequencing platform.

18. The method of claim 17, wherein:
the Tn5 transposase enzyme loaded with amplification-blocked primary adapters is present in a tagmentation buffer, optionally wherein the Tn5 enzyme loaded with amplification-blocker primary adapters in the tagmentation buffer contacts the cells or tissue sample for about 20 minutes to about 16 hours, optionally wherein the Tn5 enzyme loaded with customized amplification-blocker primary adapters in the tagmentation buffer contacts the cells or tissue sample at between about 25° C. and about 55° C., optionally wherein the buffer contacts the cells or tissue sample for about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, or about 16 hours;
the cells or tissue sample is obtained from a tissue selected from the group consisting of brain, lung, liver, kidney, pancreas, heart, and gastrointestinal (GI) tract;
the cells or tissue sample is obtained from a tumor;
the subject is a mammal, optionally a human; and/or
the sequencing platform is an NGS platform.

* * * * *

SEQUENCE LISTING

<160> NUMBER OF SEQ ID NOS: 10

<210> SEQ ID NO 1
<211> LENGTH: 33
<212> TYPE: DNA
<213> ORGANISM: Artificial
<220> FEATURE:
<223> OTHER INFORMATION: Synthetic

<400> SEQUENCE: 1
tcgtcggcag cgtcagatgt gtataagaga cag         33

<210> SEQ ID NO 2
<211> LENGTH: 34
<212> TYPE: DNA
<213> ORGANISM: Artificial
<220> FEATURE:
<223> OTHER INFORMATION: Synthetic

<400> SEQUENCE: 2
gtctcgtggg ctcggagatg tgtataagag acag        34

<210> SEQ ID NO 3
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(19)
<223> OTHER INFORMATION: n is a, c, g, or t

<400> SEQUENCE: 3
nnnnnnnnnn nnnnnnnnnt gtataagaga cag         33

<210> SEQ ID NO 4
<211> LENGTH: 37
<212> TYPE: DNA
<213> ORGANISM: Artificial
<220> FEATURE:
<223> OTHER INFORMATION: Synthetic

<400> SEQUENCE: 4
aatgatacgg cgaccaccga gatctacacc tctctat     37

<210> SEQ ID NO 5
<211> LENGTH: 43
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (25)..(32)
<223> OTHER INFORMATION: n is a, c, g, or t

<400> SEQUENCE: 5
caagcagaag acggcatacg agatnnnnnn nncgactgac tct    43

<210> SEQ ID NO 6
<211> LENGTH: 24
<212> TYPE: DNA
<213> ORGANISM: Artificial
<220> FEATURE:
<223> OTHER INFORMATION: Synthetic

<400> SEQUENCE: 6

```
tgccgacgaa tagagaggtg tagc                                              24

<210> SEQ ID NO 7
<211> LENGTH: 22
<212> TYPE: DNA
<213> ORGANISM: Artificial
<220> FEATURE:
<223> OTHER INFORMATION: Synthetic

<400> SEQUENCE: 7
cccacgagac agagtcagtc gc                                                22

<210> SEQ ID NO 8
<211> LENGTH: 15
<212> TYPE: DNA
<213> ORGANISM: Artificial
<220> FEATURE:
<223> OTHER INFORMATION: Synthetic

<400> SEQUENCE: 8
ctgtctctta tacac                                                        15

<210> SEQ ID NO 9
<211> LENGTH: 29
<212> TYPE: DNA
<213> ORGANISM: Artificial
<220> FEATURE:
<223> OTHER INFORMATION: Synthetic

<400> SEQUENCE: 9
aatgatacgg cgaccaccga gatctacac                                         29

<210> SEQ ID NO 10
<211> LENGTH: 24
<212> TYPE: DNA
<213> ORGANISM: Artificial
<220> FEATURE:
<223> OTHER INFORMATION: Synthetic

<400> SEQUENCE: 10
caagcagaag acggcatacg agat                                              24
```